United States Patent
Atwell et al.

(10) Patent No.: US 10,604,573 B2
(45) Date of Patent: Mar. 31, 2020

(54) BTLA AGONIST ANTIBODIES AND USES THEREOF

(71) Applicant: Eli Lilly and Company, Indianapolis, IN (US)

(72) Inventors: Shane Krummen Atwell, Carlsbad, CA (US); Andrew Charles Vendel, San Diego, CA (US); Victor H. Obungu, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 95 days.

(21) Appl. No.: 15/977,003

(22) Filed: May 11, 2018

(65) Prior Publication Data

US 2018/0334502 A1  Nov. 22, 2018

Related U.S. Application Data

(60) Provisional application No. 62/508,510, filed on May 19, 2017.

(51) Int. Cl.
  *C07K 16/00*  (2006.01)
  *C12P 21/08*  (2006.01)
  *C07K 16/28*  (2006.01)

(52) U.S. Cl.
  CPC ...... *C07K 16/2818* (2013.01); *C07K 2317/14* (2013.01); *C07K 2317/34* (2013.01); *C07K 2317/51* (2013.01); *C07K 2317/515* (2013.01); *C07K 2317/56* (2013.01); *C07K 2317/565* (2013.01); *C07K 2317/73* (2013.01); *C07K 2317/75* (2013.01); *C07K 2317/92* (2013.01)

(58) Field of Classification Search
None
See application file for complete search history.

(56) References Cited

U.S. PATENT DOCUMENTS

| 8,546,541 | B2 | 10/2013 | Murphy et al. |
| 8,563,694 | B2 | 10/2013 | Mataraza et al. |
| 9,045,562 | B2 | 6/2015 | Murphy et al. |

FOREIGN PATENT DOCUMENTS

| WO | 2011014438 A1 | 2/2011 |
| WO | 2016176583 A1 | 11/2016 |
| WO | 2017/096017 A1 | 6/2017 |

OTHER PUBLICATIONS

Okano M, et al. 2008. *Clin. Exp. Allergy* 38:1891.
Otsuki N, et al. 2006. *Biochem. Bioph. Res. Co.* 344:1121.
Govindarajan Thangavelu, et al: "divide and conquer: Blocking graft versus host but not graft versus leukemia T cells with agonist BTLA co-inhibitory signals", Chimerism, vol. 2, No. , Jan. 1, 2011.
Jrn C. Albring, et al: "Targeting of B and T lymphocyte associated (BTLA) prevents graft-versus-host disease without global immunosuppression", The Journal of Experimental Medicine, vol. 207, No. 12, Nov. 22, 2010.

*Primary Examiner* — Amy E Juedes
(74) *Attorney, Agent, or Firm* — Xiaoguang Gao

(57) ABSTRACT

Antibodies which bind BTLA, and methods of using same, are provided, said antibodies are useful as agents for treating conditions associated with autoimmune disease including treating lupus.

9 Claims, No Drawings
Specification includes a Sequence Listing.

SEQUENCE LISTING

<160> NUMBER OF SEQ ID NOS: 41

<210> SEQ ID NO 1
<211> LENGTH: 449
<212> TYPE: PRT
<213> ORGANISM: Artificial Sequence
<220> FEATURE:
<223> OTHER INFORMATION: Synthetic Construct

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Phe Ser Leu Ser Ser Tyr
            20                  25                  30

Gly Val Ser Trp Val Arg Gln Ala Pro Gly Gln Gly Leu Glu Trp Met
        35                  40                  45

Gly Ala Ile Ser Tyr Asp Gly Ile Thr Tyr Tyr Ala Ser Trp Ala Lys
    50                  55                  60

Ser Arg Val Thr Met Thr Arg Asp Thr Ser Thr Ser Thr Val Tyr Met
65                  70                  75                  80

Glu Leu Ser Ser Leu Arg Ser Glu Asp Thr Ala Val Tyr Tyr Cys Ala
                85                  90                  95

Arg Gly Asp Tyr Tyr Asp Tyr Val Tyr Tyr Val Tyr Ala Leu Asp Ile
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val

```
            145                 150                 155                 160
        Thr Val Ser Trp Asn Ser Gly Ala Leu Thr Ser Gly Val His Thr Phe
                        165                 170                 175

Pro Ala Val Leu Gln Ser Ser Gly Leu Tyr Ser Leu Ser Ser Val Val
                        180                 185                 190

Thr Val Pro Ser Ser Leu Gly Thr Lys Thr Tyr Thr Cys Asn Val
                    195                 200                 205

Asp His Lys Pro Ser Asn Thr Lys Val Asp Lys Arg Val Glu Ser Lys
                210                 215                 220

Tyr Gly Pro Pro Cys Pro Cys Pro Ala Pro Glu Ala Ala Gly Gly
        225                 230                 235                 240

Pro Ser Val Phe Leu Phe Pro Pro Lys Pro Lys Asp Thr Leu Met Ile
                        245                 250                 255

Ser Arg Thr Pro Glu Val Thr Cys Val Val Val Asp Val Ser Gln Glu
                    260                 265                 270

Asp Pro Glu Val Gln Phe Asn Trp Tyr Val Asp Gly Val Glu Val His
                    275                 280                 285

Asn Ala Lys Thr Lys Pro Arg Glu Glu Gln Phe Asn Ser Thr Tyr Arg
                290                 295                 300

Val Val Ser Val Leu Thr Val Leu His Gln Asp Trp Leu Asn Gly Lys
        305                 310                 315                 320

Glu Tyr Lys Cys Lys Val Ser Asn Lys Gly Leu Pro Ser Ser Ile Glu
                        325                 330                 335

Lys Thr Ile Ser Lys Ala Lys Gly Gln Pro Arg Glu Pro Gln Val Tyr
                    340                 345                 350

Thr Leu Pro Pro Ser Gln Glu Glu Met Thr Lys Asn Gln Val Ser Leu
                    355                 360                 365

Thr Cys Leu Val Lys Gly Phe Tyr Pro Ser Asp Ile Ala Val Glu Trp
                370                 375                 380

Glu Ser Asn Gly Gln Pro Glu Asn Asn Tyr Lys Thr Thr Pro Pro Val
        385                 390                 395                 400

Leu Asp Ser Asp Gly Ser Phe Phe Leu Tyr Ser Arg Leu Thr Val Asp
                        405                 410                 415

Lys Ser Arg Trp Gln Glu Gly Asn Val Phe Ser Cys Ser Val Met His
                        420                 425                 430

Glu Ala Leu His Asn His Tyr Thr Gln Lys Ser Leu Ser Leu Ser Leu
                    435                 440                 445

Gly

<210> SEQ ID NO 2
<211> LENGTH: 217
<212> TYPE: PRT
<213> ORGANISM: Artificial Sequence
<220> FEATURE:
<223> OTHER INFORMATION: Synthetic Construct

<400> SEQUENCE: 2

Glu Ile Val Leu Thr Gln Ser Pro Gly Thr Leu Ser Leu Ser Pro Gly
        1               5                   10                  15

Glu Arg Ala Thr Leu Ser Cys Gln Ala Ser Gln Ser Ile Ser Thr Ala
                    20                  25                  30

Leu Ala Trp Tyr Gln Gln Lys Pro Gly Gln Ala Pro Arg Leu Leu Ile
                35                  40                  45

Tyr Ala Ala Ser Thr Leu Ala Ser Gly Ile Pro Asp Arg Phe Ser Gly
            50                  55                  60
```

```
Ser Gly Ser Gly Thr Asp Phe Thr Leu Thr Ile Ser Arg Leu Glu Pro
 65                  70                  75                  80

Glu Asp Phe Ala Val Tyr Tyr Cys Gln Gln Gly Tyr Ser Ser Ser Asn
                 85                  90                  95

Leu Asp Asn Val Phe Gly Gly Thr Lys Val Glu Ile Lys Arg Thr
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 3
<211> LENGTH: 123
<212> TYPE: PRT
<213> ORGANISM: Artificial Sequence
<220> FEATURE:
<223> OTHER INFORMATION: Synthetic Construct

<400> SEQUENCE: 3

Gln Val Gln Leu Val Gln Ser Gly Ala Glu Val Lys Lys Pro Gly Ala
 1               5                  10                  15

Ser Val Lys Val Ser Cys Lys Ala Ser Gly Phe Ser Leu Ser Ser Tyr
            20                  25                  30

Gly Val Ser Trp Val Arg Gln Ala Pro Gly Gln Gly Leu Glu Trp Met
        35                  40                  45

Gly Ala Ile Ser Tyr Asp Gly Ile Thr Tyr Tyr Ala Ser Trp Ala Lys
    50                  55                  60

Ser Arg Val Thr Met Thr Arg Asp Thr Ser Thr Ser Thr Val Tyr Met
 65                  70                  75                  80

Glu Leu Ser Ser Leu Arg Ser Glu Asp Thr Ala Val Tyr Tyr Cys Ala
                 85                  90                  95

Arg Gly Asp Tyr Tyr Asp Asp Tyr Val Tyr Val Tyr Ala Leu Asp Ile
            100                 105                 110

Trp Gly Gln Gly Thr Leu Val Thr Val Ser Ser
        115                 120

<210> SEQ ID NO 4
<211> LENGTH: 110
<212> TYPE: PRT
<213> ORGANISM: Artificial Sequence
<220> FEATURE:
<223> OTHER INFORMATION: Synthetic Construct

<400> SEQUENCE: 4

Glu Ile Val Leu Thr Gln Ser Pro Gly Thr Leu Ser Leu Ser Pro Gly
 1               5                  10                  15

Glu Arg Ala Thr Leu Ser Cys Gln Ala Ser Gln Ser Ile Ser Thr Ala
```

```
                20                  25                  30
Leu Ala Trp Tyr Gln Gln Lys Pro Gly Gln Ala Pro Arg Leu Leu Ile
            35                  40                  45

Tyr Ala Ala Ser Thr Leu Ala Ser Gly Ile Pro Asp Arg Phe Ser Gly
        50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Gly Tyr Ser Ser Ser Asn
                85                  90                  95

Leu Asp Asn Val Phe Gly Gly Gly Thr Lys Val Glu Ile Lys
            100                 105                 110

<210> SEQ ID NO 5
<211> LENGTH: 441
<212> TYPE: PRT
<213> ORGANISM: Artificial Sequence
<220> FEATURE:
<223> OTHER INFORMATION: Synthetic Construct

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Ile Ser Lys Tyr
            20                  25                  30

Asn Ile Gln Trp Val Arg Gln Ala Pro Gly Lys Gly Leu Glu Trp Val
        35                  40                  45

Gly Phe Ile Asn Tyr Gly Gly Ser Ala Tyr Tyr Ala Ser Arg Ala Lys
    50                  55                  60

Gly Arg Phe Thr Ile Ser Arg Asp Asp Ser Lys Asn Ser Leu Tyr Leu
65                  70                  75                  80

Gln Met Asn Ser Leu Lys Thr Glu Asp Thr Ala Val Tyr Tyr Cys Ala
                85                  90                  95

Arg Gly Leu Ser Asn Ser Asp Leu Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
    210                 215                 220

Pro Ala Pro Glu Ala Ala Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
```

```
                275                 280                 285
Glu Gln Phe Asn Ser Thr Tyr Arg Val Val Ser Val Leu Thr Val Leu
            290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
                355                 360                 365

Pro Ser Asp Ile Ala Val Glu Trp Glu Ser Asn Gly Gln Pro Glu Asn
            370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly
                435                 440

<210> SEQ ID NO 6
<211> LENGTH: 221
<212> TYPE: PRT
<213> ORGANISM: Artificial Sequence
<220> FEATURE:
<223> OTHER INFORMATION: Synthetic Construct

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Trp
                20                  25                  30

Leu Ser Trp Tyr Gln Gln Lys Pro Gly Lys Ala Pro Lys Leu Leu Ile
            35                  40                  45

Tyr Arg Ala Ser Thr Leu Ala Ser Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Ser Thr Tyr Gly Gly Val Val
                85                  90                  95

Gly Ser Thr Ser Asp Asp Asn Pro Phe Gly Gly Gly Thr Lys Val Glu
            100                 105                 110

Ile Lys Arg Thr Val Ala Ala Pro Ser Val Phe Ile Phe Pro Pro Ser
        115                 120                 125

Asp Glu Gln Leu Lys Ser Gly Thr Ala Ser Val Cys Leu Leu Asn
                130                 135                 140

Asn Phe Tyr Pro Arg Glu Ala Lys Val Gln Trp Lys Val Asp Asn Ala
145                 150                 155                 160

Leu Gln Ser Gly Asn Ser Gln Glu Ser Val Thr Glu Gln Asp Ser Lys
                165                 170                 175

Asp Ser Thr Tyr Ser Leu Ser Ser Thr Leu Thr Leu Ser Lys Ala Asp
            180                 185                 190

Tyr Glu Lys His Lys Val Tyr Ala Cys Glu Val Thr His Gln Gly Leu
```

```
                195                 200                 205
Ser Ser Pro Val Thr Lys Ser Phe Asn Arg Gly Glu Cys
    210                 215                 220

<210> SEQ ID NO 7
<211> LENGTH: 115
<212> TYPE: PRT
<213> ORGANISM: Artificial Sequence
<220> FEATURE:
<223> OTHER INFORMATION: Synthetic Construct

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Ile Ser Lys Tyr
            20                  25                  30

Asn Ile Gln Trp Val Arg Gln Ala Pro Gly Lys Gly Leu Glu Trp Val
        35                  40                  45

Gly Phe Ile Asn Tyr Gly Gly Ser Ala Tyr Tyr Ala Ser Arg Ala Lys
    50                  55                  60

Gly Arg Phe Thr Ile Ser Arg Asp Asp Ser Lys Asn Ser Leu Tyr Leu
65                  70                  75                  80

Gln Met Asn Ser Leu Lys Thr Glu Asp Thr Ala Val Tyr Tyr Cys Ala
                85                  90                  95

Arg Gly Leu Ser Asn Ser Asp Leu Trp Gly Gln Gly Thr Leu Val Thr
            100                 105                 110

Val Ser Ser
        115

<210> SEQ ID NO 8
<211> LENGTH: 114
<212> TYPE: PRT
<213> ORGANISM: Artificial Sequence
<220> FEATURE:
<223> OTHER INFORMATION: Synthetic Construct

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Ser Trp
            20                  25                  30

Leu Ser Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Ser Thr Tyr Gly Gly Val Val
                85                  90                  95

Gly Ser Thr Ser Asp Asp Asn Pro Phe Gly Gly Gly Thr Lys Val Glu
            100                 105                 110

Ile Lys

<210> SEQ ID NO 9
<211> LENGTH: 447
<212> TYPE: PRT
<213> ORGANISM: Artificial Sequence
<220> FEATURE:
<223> OTHER INFORMATION: Synthetic Construct
```

<400> SEQUENCE: 9

```
Gln Val Gln Leu Val Gln Ser Gly Ala Glu Val Lys Lys Pro Gly Ala
1               5                   10                  15

Ser Val Lys Val Ser Cys Lys Ala Ser Gly Phe Ser Leu Ser Thr Tyr
            20                  25                  30

Ala Met Asn Trp Val Arg Gln Ala Pro Gly Gln Gly Leu Glu Trp Met
        35                  40                  45

Gly Ile Ile Ser Asp Asp Gly Thr Thr Tyr Tyr Ala Thr Trp Ala Lys
50                  55                  60

Gly Arg Val Thr Met Thr Arg Asp Thr Ser Thr Ser Thr Val Tyr Met
65                  70                  75                  80

Glu Leu Ser Ser Leu Arg Ser Glu Asp Thr Ala Val Tyr Tyr Cys Ala
                85                  90                  95

Arg Asp Ala Gly Ala Gly Val Gln Asp Tyr Leu Thr Leu Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
210                 215                 220

Pro Pro Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
```

```
                    405                 410                 415
Arg Trp Gln Glu Gly Asn Val Phe Ser Cys Ser Val Met His Glu Ala
                420                 425                 430

Leu His Asn His Tyr Thr Gln Lys Ser Leu Ser Leu Ser Leu Gly
            435                 440                 445

<210> SEQ ID NO 10
<211> LENGTH: 217
<212> TYPE: PRT
<213> ORGANISM: Artificial Sequence
<220> FEATURE:
<223> OTHER INFORMATION: Synthetic Construct

<400> SEQUENCE: 10

Asp Ile Val Met Thr Gln Ser Pro Asp Ser Leu Ala Val Ser Leu Gly
1               5                   10                  15

Glu Arg Ala Thr Ile Asn Cys Gln Ala Ser Glu Asn Ile Tyr Asn Phe
            20                  25                  30

Leu Ala Trp Tyr Gln Gln Lys Pro Gly Gln Pro Pro Lys Leu Leu Ile
        35                  40                  45

Tyr Ser Ala Ser Thr Leu Ala Ser Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Gly Ser Ser Asn Ser Asn
                85                  90                  95

Ile Asp Asn Pro Phe Gly Gly Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 11
<211> LENGTH: 121
<212> TYPE: PRT
<213> ORGANISM: Artificial Sequence
<220> FEATURE:
<223> OTHER INFORMATION: Synthetic Construct

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Phe Ser Leu Ser Thr Tyr
            20                  25                  30

Ala Met Asn Trp Val Arg Gln Ala Pro Gly Gln Gly Leu Glu Trp Met
        35                  40                  45
```

```
Gly Ile Ile Ser Asp Asp Gly Thr Thr Tyr Tyr Ala Thr Trp Ala Lys
        50                  55                  60

Gly Arg Val Thr Met Thr Arg Asp Thr Ser Thr Ser Thr Val Tyr Met
65                  70                  75                  80

Glu Leu Ser Ser Leu Arg Ser Glu Asp Thr Ala Val Tyr Tyr Cys Ala
                85                  90                  95

Arg Asp Ala Gly Ala Gly Gly Val Gln Asp Tyr Leu Thr Leu Trp Gly
            100                 105                 110

Gln Gly Thr Leu Val Thr Val Ser Ser
        115                 120
```

<210> SEQ ID NO 12
<211> LENGTH: 110
<212> TYPE: PRT
<213> ORGANISM: Artificial Sequence
<220> FEATURE:
<223> OTHER INFORMATION: Synthetic Construct

<400> SEQUENCE: 12

```
Asp Ile Val Met Thr Gln Ser Pro Asp Ser Leu Ala Val Ser Leu Gly
1               5                   10                  15

Glu Arg Ala Thr Ile Asn Cys Gln Ala Ser Glu Asn Ile Tyr Asn Phe
            20                  25                  30

Leu Ala Trp Tyr Gln Gln Lys Pro Gly Gln Pro Pro Lys Leu Leu Ile
        35                  40                  45

Tyr Ser Ala Ser Thr Leu Ala Ser Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln Gly Ser Ser Asn Ser Asn
                85                  90                  95

Ile Asp Asn Pro Phe Gly Gly Gly Thr Lys Val Glu Ile Lys
            100                 105                 110
```

<210> SEQ ID NO 13
<211> LENGTH: 10
<212> TYPE: PRT
<213> ORGANISM: Artificial Sequence
<220> FEATURE:
<223> OTHER INFORMATION: Synthetic Construct

<400> SEQUENCE: 13

```
Gly Phe Ser Leu Ser Ser Tyr Gly Val Ser
1               5                   10
```

<210> SEQ ID NO 14
<211> LENGTH: 10
<212> TYPE: PRT
<213> ORGANISM: Artificial Sequence
<220> FEATURE:
<223> OTHER INFORMATION: Synthetic Construct

<400> SEQUENCE: 14

```
Gly Phe Asp Ile Ser Lys Tyr Asn Ile Gln
1               5                   10
```

<210> SEQ ID NO 15
<211> LENGTH: 10
<212> TYPE: PRT
<213> ORGANISM: Artificial Sequence
<220> FEATURE:
<223> OTHER INFORMATION: Synthetic Construct

```
<400> SEQUENCE: 15

Gly Phe Ser Leu Ser Thr Tyr Ala Met Asn
1               5                   10

<210> SEQ ID NO 16
<211> LENGTH: 16
<212> TYPE: PRT
<213> ORGANISM: Artificial Sequence
<220> FEATURE:
<223> OTHER INFORMATION: Synthetic Construct

<400> SEQUENCE: 16

Ala Ile Ser Tyr Asp Gly Ile Thr Tyr Tyr Ala Ser Trp Ala Lys Ser
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Synthetic Construct

<400> SEQUENCE: 17

Phe Ile Asn Tyr Gly Gly Ser Ala Tyr Tyr Ala Ser Arg Ala Lys Gly
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Synthetic Construct

<400> SEQUENCE: 18

Ile Ile Ser Asp Asp Gly Thr Thr Tyr Tyr Ala Thr Trp Ala Lys Gly
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: Synthetic Construct

<400> SEQUENCE: 19

Gly Asp Tyr Tyr Asp Asp Tyr Val Tyr Val Tyr Ala Leu Asp Ile
1               5                   10                  15

<210> SEQ ID NO 20
<211> LENGTH: 7
<212> TYPE: PRT
<213> ORGANISM: Artificial Sequence
<220> FEATURE:
<223> OTHER INFORMATION: Synthetic Construct

<400> SEQUENCE: 20

Gly Leu Ser Asn Ser Asp Leu
1               5

<210> SEQ ID NO 21
<211> LENGTH: 13
<212> TYPE: PRT
<213> ORGANISM: Artificial Sequence
<220> FEATURE:
<223> OTHER INFORMATION: Synthetic Construct
```

```
<400> SEQUENCE: 21

Asp Ala Gly Ala Gly Gly Val Gln Asp Tyr Leu Thr Leu
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Synthetic Construct

<400> SEQUENCE: 22

Gln Ala Ser Gln Ser Ile Ser Thr Ala Leu Ala
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Synthetic Construct

<400> SEQUENCE: 23

Gln Ala Ser Gln Ser Ile Ser Ser Trp Leu Ser
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Synthetic Construct

<400> SEQUENCE: 24

Gln Ala Ser Glu Asn Ile Tyr Asn Phe Leu Ala
1               5                   10

<210> SEQ ID NO 25
<211> LENGTH: 7
<212> TYPE: PRT
<213> ORGANISM: Artificial Sequence
<220> FEATURE:
<223> OTHER INFORMATION: Synthetic Construct

<400> SEQUENCE: 25

Ala Ala Ser Thr Leu Ala Ser
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic Construct

<400> SEQUENCE: 26

Arg Ala Ser Thr Leu Ala Ser
1               5

<210> SEQ ID NO 27
<211> LENGTH: 7
<212> TYPE: PRT
<213> ORGANISM: Artificial Sequence
<220> FEATURE:
<223> OTHER INFORMATION: Synthetic Construct

<400> SEQUENCE: 27
```

```
Ser Ala Ser Thr Leu Ala Ser
1               5

<210> SEQ ID NO 28
<211> LENGTH: 12
<212> TYPE: PRT
<213> ORGANISM: Artificial Sequence
<220> FEATURE:
<223> OTHER INFORMATION: Synthetic Construct

<400> SEQUENCE: 28

Gln Gln Gly Tyr Ser Ser Ser Asn Leu Asp Asn Val
1               5                   10

<210> SEQ ID NO 29
<211> LENGTH: 16
<212> TYPE: PRT
<213> ORGANISM: Artificial Sequence
<220> FEATURE:
<223> OTHER INFORMATION: Synthetic Construct

<400> SEQUENCE: 29

Gln Ser Thr Tyr Gly Gly Val Val Gly Ser Thr Ser Asp Asp Asn Pro
1               5                   10                  15

<210> SEQ ID NO 30
<211> LENGTH: 12
<212> TYPE: PRT
<213> ORGANISM: Artificial Sequence
<220> FEATURE:
<223> OTHER INFORMATION: Synthetic Construct

<400> SEQUENCE: 30

Gln Gln Gly Ser Ser Asn Ser Asn Ile Asp Asn Pro
1               5                   10

<210> SEQ ID NO 31
<211> LENGTH: 289
<212> TYPE: PRT
<213> ORGANISM: Homo sapiens

<400> SEQUENCE: 31

Met Lys Thr Leu Pro Ala Met Leu Gly Thr Gly Lys Leu Phe Trp Val
1               5                   10                  15

Phe Phe Leu Ile Pro Tyr Leu Asp Ile Trp Asn Ile His Gly Lys Glu
                20                  25                  30

Ser Cys Asp Val Gln Leu Tyr Ile Lys Arg Gln Ser Glu His Ser Ile
            35                  40                  45

Leu Ala Gly Asp Pro Phe Glu Leu Glu Cys Pro Val Lys Tyr Cys Ala
        50                  55                  60

Asn Arg Pro His Val Thr Trp Cys Lys Leu Asn Gly Thr Thr Cys Val
65                  70                  75                  80

Lys Leu Glu Asp Arg Gln Thr Ser Trp Lys Glu Lys Asn Ile Ser
                85                  90                  95

Phe Phe Ile Leu His Phe Glu Pro Val Leu Pro Asn Asp Asn Gly Ser
                100                 105                 110

Tyr Arg Cys Ser Ala Asn Phe Gln Ser Asn Leu Ile Glu Ser His Ser
            115                 120                 125

Thr Thr Leu Tyr Val Thr Asp Val Lys Ser Ala Ser Glu Arg Pro Ser
        130                 135                 140

Lys Asp Glu Met Ala Ser Arg Pro Trp Leu Leu Tyr Arg Leu Leu Pro
```

```
145                 150                 155                 160
Leu Gly Gly Leu Pro Leu Leu Ile Thr Thr Cys Phe Cys Leu Phe Cys
                165                 170                 175
Cys Leu Arg Arg His Gln Gly Lys Gln Asn Glu Leu Ser Asp Thr Ala
                180                 185                 190
Gly Arg Glu Ile Asn Leu Val Asp Ala His Leu Lys Ser Glu Gln Thr
                195                 200                 205
Glu Ala Ser Thr Arg Gln Asn Ser Gln Val Leu Leu Ser Glu Thr Gly
                210                 215                 220
Ile Tyr Asp Asn Asp Pro Asp Leu Cys Phe Arg Met Gln Glu Gly Ser
225                 230                 235                 240
Glu Val Tyr Ser Asn Pro Cys Leu Glu Glu Asn Lys Pro Gly Ile Val
                245                 250                 255
Tyr Ala Ser Leu Asn His Ser Val Ile Gly Pro Asn Ser Arg Leu Ala
                260                 265                 270
Arg Asn Val Lys Glu Ala Pro Thr Glu Tyr Ala Ser Ile Cys Val Arg
                275                 280                 285
Ser

<210> SEQ ID NO 32
<211> LENGTH: 306
<212> TYPE: PRT
<213> ORGANISM: Mus musculus

<400> SEQUENCE: 32

Met Lys Thr Val Pro Ala Met Leu Gly Thr Pro Arg Leu Phe Arg Glu
1               5                   10                  15
Phe Phe Ile Leu His Leu Gly Leu Trp Ser Ile Leu Cys Glu Lys Ala
                20                  25                  30
Thr Lys Arg Asn Asp Glu Glu Cys Glu Val Gln Leu Asn Ile Lys Arg
                35                  40                  45
Asn Ser Lys His Ser Ala Trp Thr Gly Glu Leu Phe Lys Ile Glu Cys
            50                  55                  60
Pro Val Lys Tyr Cys Val His Arg Pro Asn Val Thr Trp Cys Lys His
65              70                  75                  80
Asn Gly Thr Ile Trp Val Pro Leu Glu Val Gly Pro Gln Leu Tyr Thr
                85                  90                  95
Ser Trp Glu Glu Asn Arg Ser Val Pro Val Phe Val Leu His Phe Lys
                100                 105                 110
Pro Ile His Leu Ser Asp Asn Gly Ser Tyr Ser Cys Ser Thr Asn Phe
                115                 120                 125
Asn Ser Gln Val Ile Asn Ser His Ser Val Thr Ile His Val Arg Glu
            130                 135                 140
Arg Thr Gln Asn Ser Ser Glu His Pro Leu Ile Thr Val Ser Asp Ile
145                 150                 155                 160
Pro Asp Ala Thr Asn Ala Ser Gly Pro Ser Thr Met Glu Glu Arg Pro
                165                 170                 175
Gly Arg Thr Trp Leu Leu Tyr Thr Leu Leu Pro Leu Gly Ala Leu Leu
                180                 185                 190
Leu Leu Leu Ala Cys Val Cys Leu Cys Phe Leu Lys Arg Ile Gln
                195                 200                 205
Gly Lys Glu Lys Lys Pro Ser Asp Leu Ala Gly Arg Asp Thr Asn Leu
            210                 215                 220
Val Asp Ile Pro Ala Ser Ser Arg Thr Asn His Gln Ala Leu Pro Ser
```

```
225                 230                 235                 240
Gly Thr Gly Ile Tyr Asp Asn Asp Pro Trp Ser Ser Met Gln Asp Glu
                245                 250                 255

Ser Glu Leu Thr Ile Ser Leu Gln Ser Glu Arg Asn Asn Gln Gly Ile
            260                 265                 270

Val Tyr Ala Ser Leu Asn His Cys Val Ile Gly Arg Asn Pro Arg Gln
        275                 280                 285

Glu Asn Asn Met Gln Glu Ala Pro Thr Glu Tyr Ala Ser Ile Cys Val
    290                 295                 300

Arg Ser
305

<210> SEQ ID NO 33
<211> LENGTH: 306
<212> TYPE: PRT
<213> ORGANISM: Mus musculus

<400> SEQUENCE: 33

Met Lys Thr Val Pro Ala Met Leu Gly Thr Pro Arg Leu Phe Arg Glu
1               5                   10                  15

Phe Phe Ile Leu His Leu Gly Leu Trp Ser Ile Leu Cys Glu Lys Ala
            20                  25                  30

Thr Lys Arg Asn Asp Glu Glu Cys Pro Val Gln Leu Thr Ile Thr Arg
        35                  40                  45

Asn Ser Lys Gln Ser Ala Arg Thr Gly Glu Leu Phe Lys Ile Gln Cys
    50                  55                  60

Pro Val Lys Tyr Cys Val His Arg Pro Asn Val Thr Trp Cys Lys His
65                  70                  75                  80

Asn Gly Thr Ile Cys Val Pro Leu Glu Val Ser Pro Gln Leu Tyr Thr
                85                  90                  95

Ser Trp Glu Glu Asn Gln Ser Val Pro Val Phe Val Leu His Phe Lys
            100                 105                 110

Pro Ile His Leu Ser Asp Asn Gly Ser Tyr Ser Cys Ser Thr Asn Phe
        115                 120                 125

Asn Ser Gln Val Ile Asn Ser His Ser Val Thr Ile His Val Thr Glu
    130                 135                 140

Arg Thr Gln Asn Ser Ser Glu His Pro Leu Ile Thr Val Ser Asp Ile
145                 150                 155                 160

Pro Asp Ala Thr Asn Ala Ser Gly Pro Ser Thr Met Glu Glu Arg Pro
                165                 170                 175

Gly Arg Thr Trp Leu Leu Tyr Thr Leu Leu Pro Leu Gly Ala Leu Leu
            180                 185                 190

Leu Leu Leu Ala Cys Val Cys Leu Leu Cys Phe Leu Lys Arg Ile Gln
        195                 200                 205

Gly Lys Glu Lys Lys Pro Ser Asp Leu Ala Gly Arg Asp Thr Asn Leu
    210                 215                 220

Val Asp Ile Pro Ala Ser Ser Arg Thr Asn His Gln Ala Leu Pro Ser
225                 230                 235                 240

Gly Thr Gly Ile Tyr Asp Asn Asp Pro Trp Ser Ser Met Gln Asp Glu
                245                 250                 255

Ser Glu Leu Thr Ile Ser Leu Gln Ser Glu Arg Asn Asn Gln Gly Ile
            260                 265                 270

Val Tyr Ala Ser Leu Asn His Cys Val Ile Gly Arg Asn Pro Arg Gln
        275                 280                 285
```

```
Glu Asn Asn Met Gln Glu Ala Pro Thr Glu Tyr Ala Ser Ile Cys Val
    290                 295                 300

Arg Ser
305

<210> SEQ ID NO 34
<211> LENGTH: 289
<212> TYPE: PRT
<213> ORGANISM: Macaca fascicularis

<400> SEQUENCE: 34

Met Lys Thr Leu Pro Ala Met Leu Gly Ser Gly Arg Leu Phe Trp Val
  1               5                  10                  15

Val Phe Leu Ile Pro Tyr Leu Asp Ile Trp Asn Ile His Gly Lys Glu
                 20                  25                  30

Ser Cys Asp Val Gln Leu Tyr Ile Lys Arg Gln Ser Tyr His Ser Ile
             35                  40                  45

Phe Ala Gly Asp Pro Phe Lys Leu Glu Cys Pro Val Lys Tyr Cys Ala
         50                  55                  60

His Arg Pro Gln Val Thr Trp Cys Lys Leu Asn Gly Thr Thr Cys Val
 65                  70                  75                  80

Lys Leu Glu Gly Arg His Thr Ser Trp Lys Gln Glu Lys Asn Leu Ser
                 85                  90                  95

Phe Phe Ile Leu His Phe Glu Pro Val Leu Pro Ser Asn Gly Ser
            100                 105                 110

Tyr Arg Cys Ser Ala Asn Phe Leu Ser Ala Ile Ile Glu Ser His Ser
            115                 120                 125

Thr Thr Leu Tyr Val Thr Asp Val Lys Ser Ala Ser Glu Arg Pro Ser
130                 135                 140

Lys Asp Glu Met Ala Ser Arg Pro Trp Leu Leu Tyr Ser Leu Leu Pro
145                 150                 155                 160

Leu Gly Gly Leu Pro Leu Leu Ile Thr Thr Cys Phe Cys Leu Phe Cys
                165                 170                 175

Phe Leu Arg Arg His Gln Gly Lys Gln Asn Glu Leu Ser Asp Thr Thr
            180                 185                 190

Gly Arg Glu Ile Thr Leu Val Asp Val Pro Phe Lys Ser Glu Gln Thr
        195                 200                 205

Glu Ala Ser Thr Arg Gln Asn Ser Gln Val Leu Leu Ser Glu Thr Gly
    210                 215                 220

Ile Tyr Asp Asn Glu Pro Asp Phe Cys Phe Arg Met Gln Glu Gly Ser
225                 230                 235                 240

Glu Val Tyr Ser Asn Pro Cys Leu Glu Glu Asn Lys Pro Gly Ile Ile
                245                 250                 255

Tyr Ala Ser Leu Asn His Ser Ile Ile Gly Leu Asn Ser Arg Gln Ala
            260                 265                 270

Arg Asn Val Lys Glu Ala Pro Thr Glu Tyr Ala Ser Ile Cys Val Arg
        275                 280                 285

Ser

<210> SEQ ID NO 35
<211> LENGTH: 1347
<212> TYPE: DNA
<213> ORGANISM: Artificial Sequence
<220> FEATURE:
<223> OTHER INFORMATION: Synthetic Construct

<400> SEQUENCE: 35
```

-continued

```
caggtgcagc tggtgcagtc tggggctgag gtgaagaagc ctggggcctc agtgaaggtt      60
tcctgcaagg catctggatt ctccctcagt agctatggaa tgagctgggt gcgacaggcc     120
cctggacaag ggcttgagtg gatgggagcc attagttatg atggtattac atactacgcg     180
agctgggcga aaagcagagt caccatgacc agggacacgt ccacgagcac agtctacatg     240
gagctgagca gcctgagatc tgaggacacg gccgtgtatt actgtgcgag aggggactac     300
tacgatgatt atgtttatgt ttatgcttta gacatctggg gccagggcac cctggtcacc     360
gtctcctcag cttctaccaa gggcccatcg gtcttccccg ctagcgccct gtccaggagc     420
acctccgaga gcacagccgc cctgggctgc ctggtcaagg actacttccc cgaaccggtg     480
acggtgtcgt ggaactcagg cgccctgacc agcggcgtgc acaccttccc ggctgtccta     540
cagtcctcag gactctactc cctcagcagc gtggtgaccg tgccctccag cagcttgggc     600
acgaagacct acacctgcaa cgtagatcac aagcccagca acaccaaggt ggacaagaga     660
gttgagtcca aatatggtcc cccatgccca ccctgcccag cacctgaggc cgccggggga     720
ccatcagtct tcctgttccc cccaaaaccc aaggacactc tcatgatctc ccggacccct     780
gaggtcacgt gcgtggtggt ggacgtgagc caggaagacc ccgaggtcca gttcaactgg     840
tacgtggatg gcgtggaggt gcataatgcc aagacaaagc cgcgggagga gcagttcaac     900
agcacgtacc gtgtggtcag cgtcctcacc gtcctgcacc aggactggct gaacggcaag     960
gagtacaagt gcaaggtctc caacaaaggc ctcccgtcct ccatcgagaa aaccatctcc    1020
aaagccaaag gcagccccg agagccacag gtgtacaccc tgcccccatc ccaggaggag    1080
atgaccaaga accaggtcag cctgacctgc ctggtcaaag gcttctaccc cagcgacatc    1140
gccgtggagt gggaaagcaa tgggcagccg gagaacaact acaagaccac gcctcccgtg    1200
ctggactccg acggctcctt cttcctctac agcaggctaa ccgtggacaa gagcaggtgg    1260
caggagggga atgtcttctc atgctccgtg atgcatgagg ctctgcacaa ccactacaca    1320
cagaagagcc tctccctgtc tctgggt                                       1347
```

<210> SEQ ID NO 36
<211> LENGTH: 651
<212> TYPE: DNA
<213> ORGANISM: Artificial Sequence
<220> FEATURE:
<223> OTHER INFORMATION: Synthetic Construct

<400> SEQUENCE: 36

```
gaaattgtgt tgacgcagtc tccaggcacc ctgtctttgt ctccagggga aagagccacc      60
ctctcctgcc aggccagtca gagcattagt actgcattag cctggtacca gcagaaacct     120
ggccaggctc ccaggctcct catctatgct gcatccactc tggcatctgg catcccagac     180
aggttcagtg gcagtgggtc tgggacagac ttcactctca ccatcagcag actggagcct     240
gaagattttg cagtgtatta ctgtcaacag ggttatagta gtagtaatct tgataatgtt     300
ttcggcggag ggaccaaggt ggagatcaaa cggaccgtgg ctgcaccatc tgtcttcatc     360
ttcccgccat ctgatgagca gttgaaatct ggaactgcct ctgttgtgtg cctgctgaat     420
aacttctatc ccagagaggc caaagtacag tggaaggtgg ataacgccct ccaatcgggt     480
aactcccagg agagtgtcac agagcaggac agcaaggaca gcacctacag cctcagcagc     540
accctgacgc tgagcaaagc agactacgag aaacacaaag tctacgcctg cgaagtcacc     600
catcagggcc tgagctcgcc cgtcacaaag agcttcaaca ggggagagtg c              651
```

<210> SEQ ID NO 37
<211> LENGTH: 1323
<212> TYPE: DNA
<213> ORGANISM: Artificial Sequence
<220> FEATURE:
<223> OTHER INFORMATION: Synthetic Construct

<400> SEQUENCE: 37

| | | | | |
|---|---|---|---|---|
| gaggtgcagc | tggtggagtc | tgggggaggc | ttggtccagc | ctggagggtc | cctgagactc | 60 |
| tcctgtgcag | cctctggatt | cgacatcagt | aagtacaaca | tccaatgggt | ccgccaggct | 120 |
| ccagggaagg | ggctggagtg | ggttggcttc | attaattatg | gtggtagcgc | atactacgcg | 180 |
| agccgggcga | aaggcagatt | caccatctca | agagatgatt | caaagaactc | actgtatctg | 240 |
| caaatgaaca | gcctgaaaac | cgaggacacg | gccgtgtatt | actgtgctag | aggactaagt | 300 |
| aatagcgacc | tctggggcca | gggcaccctg | gtcaccgtct | cctcagcttc | taccaagggc | 360 |
| ccatcggtct | tccccgctagc | gcctgctcc | aggagcacct | ccgagagcac | agccgccctg | 420 |
| ggctgcctgg | tcaaggacta | cttccccgaa | ccggtgacgg | tgtcgtggaa | ctcaggcgcc | 480 |
| ctgaccagcg | gcgtgcacac | cttcccggct | gtcctacagt | cctcaggact | ctactccctc | 540 |
| agcagcgtgg | tgaccgtgcc | ctccagcagc | ttgggcacga | agacctacac | ctgcaacgta | 600 |
| gatcacaagc | ccagcaacac | caaggtggac | aagagagttg | agtccaaata | tggtccccca | 660 |
| tgcccaccct | gcccagcacc | tgaggccgcc | ggggaccat | cagtcttcct | gttccccca | 720 |
| aaacccaagg | acactctcat | gatctcccgg | accctgagg | tcacgtgcgt | ggtggtggac | 780 |
| gtgagccagg | aagaccccga | ggtccagttc | aactggtacg | tggatggcgt | ggaggtgcat | 840 |
| aatgccaaga | caaagccgcg | ggaggagcag | ttcaacagca | cgtaccgtgt | ggtcagcgtc | 900 |
| ctcaccgtcc | tgcaccagga | ctggctgaac | ggcaaggagt | acaagtgcaa | ggtctccaac | 960 |
| aaaggcctcc | cgtcctccat | cgagaaaacc | atctccaaag | ccaaagggca | gccccgagag | 1020 |
| ccacaggtgt | acaccctgcc | cccatcccag | gaggagatga | ccaagaacca | ggtcagcctg | 1080 |
| acctgcctgg | tcaaaggctt | ctaccccagc | gacatcgccg | tggagtggga | aagcaatggg | 1140 |
| cagccggaga | acaactacaa | gaccacgcct | cccgtgctgg | actccgacgg | ctccttcttc | 1200 |
| ctctacagca | ggctaaccgt | ggacaagagc | aggtggcagg | aggggaatgt | cttctcatgc | 1260 |
| tccgtgatgc | atgaggctct | gcacaaccac | tacacacaga | agagcctctc | cctgtctctg | 1320 |
| ggt | | | | | | 1323 |

<210> SEQ ID NO 38
<211> LENGTH: 663
<212> TYPE: DNA
<213> ORGANISM: Artificial Sequence
<220> FEATURE:
<223> OTHER INFORMATION: Synthetic Construct

<400> SEQUENCE: 38

| | | | | | | |
|---|---|---|---|---|---|---|
| gacatccaga | tgacccagtc | tccatcctcc | ctgtctgcat | ctgtaggaga | cagagtcacc | 60 |
| atcacttgcc | aggccagtca | gagcattagt | agttggttat | cctggtatca | gcagaaacca | 120 |
| gggaaagccc | ctaagctcct | gatctacagg | gcatccactc | tggcatctgg | ggtcccatca | 180 |
| aggttcagtg | gaagtggatc | tgggacagat | tttactttca | ccatcagcag | cctgcagcct | 240 |
| gaagatattg | caacatatta | ctgtcaatcc | acttatggtg | gtgttgttgg | cagtactagt | 300 |
| gatgataatc | ctttcggcgg | agggaccaag | gtggagatca | aacggaccgt | ggctgcacca | 360 |
| tctgtcttca | tcttcccgcc | atctgatgag | cagttgaaat | ctggaactgc | ctctgttgtg | 420 |

```
tgcctgctga ataacttcta tcccagagag gccaaagtac agtggaaggt ggataacgcc      480
ctccaatcgg gtaactccca ggagagtgtc acagagcagg acagcaagga cagcacctac      540
agcctcagca gcaccctgac gctgagcaaa gcagactacg agaaacacaa agtctacgcc      600
tgcgaagtca cccatcaggg cctgagctcg cccgtcacaa agagcttcaa caggggagag      660
tgc                                                                    663
```

<210> SEQ ID NO 39
<211> LENGTH: 1341
<212> TYPE: DNA
<213> ORGANISM: Artificial Sequence
<220> FEATURE:
<223> OTHER INFORMATION: Synthetic Construct

<400> SEQUENCE: 39

```
caggtgcagc tggtgcagtc tggggctgag gtgaagaagc ctggggcctc agtgaaggtt       60
tcctgcaagg catctggatt ctccctcagt acctatgcaa tgaactgggt gcgacaggcc      120
cctggacaag gcttgagtg gatgggaatc attagtgatg atggtaccac atactacgcg      180
acctgggcga aaggcagagt caccatgacc agggacacgt ccacgagcac agtctacatg      240
gagctgagca gcctgagatc tgaggacacg gccgtgtatt actgtgcgag agatgctggt      300
gctggtggtg tccaagacta cttaaccttg tggggccagg gcaccctggt caccgtctcc      360
tcagcttcta ccaagggccc atcggtcttc ccgctagcgc cctgctccag gagcacctcc      420
gagagcacag ccgccctggg ctgcctggtc aaggactact ccccgaacc ggtgacggtg       480 tcgtggaact caggcgccct gaccagcggc gtgcacacct tcccggctgt cctacagtcc      540
tcaggactct actccctcag cagcgtggtg accgtgccct ccagcagctt gggcacgaag      600
acctacacct gcaacgtaga tcacaagccc agcaacacca aggtggacaa gagagttgag      660
tccaaatatg gtcccccatg cccacccctgc ccagcacctg aggccgccgg gggaccatca      720
gtcttcctgt tccccccaaa acccaaggac actctcatga tctcccggac ccctgaggtc      780
acgtgcgtgg tggtggacgt gagccaggaa gaccccgagg tccagttcaa ctggtacgtg      840
gatggcgtgg aggtgcataa tgccaagaca aagccgcggg aggagcagtt caacagcacg      900
taccgtgtgg tcagcgtcct caccgtcctg caccaggact ggctgaacgg caaggagtac      960
aagtgcaagg tctccaacaa aggcctcccg tcctccatcg agaaaaccat ctccaaagcc     1020
aaagggcagc cccgagagcc acaggtgtac accctgcccc catcccagga ggagatgacc     1080
aagaaccagg tcagcctgac ctgcctggtc aaaggcttct accccagcga catcgccgtg     1140
gagtgggaaa gcaatgggca gccggagaac aactacaaga ccacgcctcc cgtgctggac     1200
tccgacggct ccttcttcct ctacagcagg ctaaccgtgg acaagagcag gtggcaggag     1260
gggaatgtct tctcatgctc cgtgatgcat gaggctctgc acaaccacta cacacagaag     1320
agcctctccc tgtctctggg t                                               1341
```

<210> SEQ ID NO 40
<211> LENGTH: 651
<212> TYPE: DNA
<213> ORGANISM: Artificial Sequence
<220> FEATURE:
<223> OTHER INFORMATION: Synthetic Construct

<400> SEQUENCE: 40

```
gacatcgtga tgacccagtc tccagactcc ctggctgtgt ctctgggcga gagggccacc       60
```

```
atcaactgcc aggccagtga gaatatttac aacttttttgg cctggtacca gcagaaacca    120
ggacagcctc ctaagctgct catttactct gcatccactc tggcatctgg ggtccctgac    180
cgattcagtg gcagcgggtc tgggacagat ttcactctca ccatcagcag cctgcaggct    240
gaagatgtgg cagtttatta ctgtcaacag ggttctagta atagtaatat tgataatcct    300
ttcggcggag ggaccaaggt ggagatcaaa cggaccgtgg ctgcaccatc tgtcttcatc    360
ttcccgccat ctgatgagca gttgaaatct ggaactgcct ctgttgtgtg cctgctgaat    420
aacttctatc ccagagaggc caaagtacag tggaaggtgg ataacgccct ccaatcgggt    480
aactcccagg agagtgtcac agagcaggac agcaaggaca gcacctacag cctcagcagc    540
accctgacgc tgagcaaagc agactacgag aaacacaaag tctacgcctg cgaagtcacc    600
catcagggcc tgagctcgcc cgtcacaaag agcttcaaca ggggagagtg c             651

<210> SEQ ID NO 41
<211> LENGTH: 283
<212> TYPE: PRT
<213> ORGANISM: Homo sapiens

<400> SEQUENCE: 41

Met Glu Pro Pro Gly Asp Trp Gly Pro Pro Trp Arg Ser Thr Pro
1               5                   10                  15

Lys Thr Asp Val Leu Arg Leu Val Leu Tyr Leu Thr Phe Leu Gly Ala
                20                  25                  30

Pro Cys Tyr Ala Pro Ala Leu Pro Ser Cys Lys Glu Asp Glu Tyr Pro
            35                  40                  45

Val Gly Ser Glu Cys Cys Pro Lys Cys Ser Pro Gly Tyr Arg Val Lys
        50                  55                  60

Glu Ala Cys Gly Glu Leu Thr Gly Thr Val Cys Glu Pro Cys Pro Pro
65                  70                  75                  80

Gly Thr Tyr Ile Ala His Leu Asn Gly Leu Ser Lys Cys Leu Gln Cys
                85                  90                  95

Gln Met Cys Asp Pro Ala Met Gly Leu Arg Ala Ser Arg Asn Cys Ser
            100                 105                 110

Arg Thr Glu Asn Ala Val Cys Gly Cys Ser Pro Gly His Phe Cys Ile
        115                 120                 125

Val Gln Asp Gly Asp His Cys Ala Ala Cys Arg Ala Tyr Ala Thr Ser
    130                 135                 140

Ser Pro Gly Gln Arg Val Gln Lys Gly Gly Thr Glu Ser Gln Asp Thr
145                 150                 155                 160

Leu Cys Gln Asn Cys Pro Pro Gly Thr Phe Ser Pro Asn Gly Thr Leu
                165                 170                 175

Glu Glu Cys Gln His Gln Thr Lys Cys Ser Trp Leu Val Thr Lys Ala
            180                 185                 190

Gly Ala Gly Thr Ser Ser Ser His Trp Val Trp Trp Phe Leu Ser Gly
        195                 200                 205

Ser Leu Val Ile Val Ile Val Cys Ser Thr Val Gly Leu Ile Ile Cys
    210                 215                 220

Val Lys Arg Arg Lys Pro Arg Gly Asp Val Val Lys Val Ile Val Ser
225                 230                 235                 240

Val Gln Arg Lys Arg Gln Glu Ala Glu Gly Glu Ala Thr Val Ile Glu
                245                 250                 255
```

```
Ala Leu Gln Ala Pro Pro Asp Val Thr Thr Val Ala Val Glu Glu Thr
            260                 265                 270

Ile Pro Ser Phe Thr Gly Arg Ser Pro Asn His
            275                 280
```

US 10,604,573 B2

BTLA AGONIST ANTIBODIES AND USES THEREOF

The present invention is in the field of medicine. More particularly, the present invention relates to antibodies directed against B and T Lymphocyte Attenuator (BTLA) and pharmaceutical compositions thereof. The antibodies of the present invention are expected to be useful in the treatment of autoimmune diseases such as lupus.

Lupus is an autoimmune disease with heterogeneous features, including skin, oral, muscle & joint, cardiac, peripheral blood, lung, kidney, reproductive, and CNS manifestations. Lupus patients are at risk for serious and life-threatening cardiovascular, renal and neuropsychiatric disease. The standard of care includes numerous steroids, which have many unfavorable and/or dangerous side effects. There is a need for therapies to manage disease and allowing for reduction or elimination of steroid use.

B and T Lymphocyte Attenuator (BTLA; CD272) is an Ig superfamily member and part of a family of checkpoint receptors that negatively regulate immune cell activation. BTLA is primarily expressed on B cells, T cells, and dendritic cells. The natural ligand for BTLA is the TNF receptor superfamily member, herpes virus entry mediator (HVEM; TNFRSF14).

Human HVEM-Fc has been reported to bind to human BTLA expressed in 293T cells with a $K_D$ of 112 nM as detected by flow cytometry. (Cheung et al., PNAS, Sep. 13, 2005, 102:37; 13218-13223). Binding of HVEM to BTLA leads to tyrosine-phosphorylation of two conserved immunoreceptor tyrosine-based inhibitory motif domains on the cytoplasmic domain of BTLA. This phosphorylation leads to recruitment of, via two Src homology 2 domains, protein tyrosine phosphatases that impart the inhibitory activity of BTLA by dephosphorylating and down-regulating positive cell receptor signaling (eg. T cell receptor or B cell receptor signal transduction cascades), thus leading to suppression of immune cell activation. In a mouse model prone to spontaneously develop lupus-like diseases (MRL-lpr mice), BTLA-deficient mice have more severe lymphocytic infiltration in salivary glands, lungs, pancreas, kidneys and joints compared to BTLA-expressing mice. Therefore, BTLA agonist antibodies may provide a benefit for patients having autoimmune diseases such as lupus.

Agonist antibodies to BTLA are known in the art. For example, U.S. Pat. No. 8,563,694 (the '694 patent) discloses BTLA agonist antibodies that either block (Mab21H6 and Mab19A7) or do not block (Mab8D5 and Mab8A3) HVEM binding to BTLA. The '694 patent describes an ongoing need to develop treatments that exploit the inhibitory role of BTLA in lymphocyte responses, while allowing for BTLA-HVEM binding. However, there is a lack of BTLA agonist antibodies that mimic the binding of HVEM to BTLA for the treatment of autoimmune diseases. An antibody "mimics" HVEM binding to BTLA if the antibody has an epitope that significantly overlaps the binding site of HVEM, and there is structural similarity between the antibody and HVEM. There is also a lack of BTLA agonist antibodies that bind human BTLA and are useful to study in in vivo pre-clinical models of autoimmune diseases such as murine and cynomolgus monkey models. Thus, there remains a need for alternative BTLA agonist antibodies.

The antibodies of the present invention seek to provide alternative BTLA agonist antibodies. Such BTLA agonist antibodies may be useful in the treatment of autoimmune diseases such as lupus. Such BTLA agonist antibodies are able to bind BTLA from multiple species such as human, cynomolgus monkey, and/or murine BTLA. In addition, such BTLA agonist antibodies demonstrate increased in vitro activity compared to an antibody having the same heavy chain variable region and light chain variable region as Mab8D5. The antibodies of the present inventions possess at least one of these desirable characteristics.

One such BTLA agonist antibody is able to bind human, cynomolgus monkey, and murine BTLA. Surprisingly, this antibody has this desired cross-reactivity because it mimics HVEM binding to BTLA. This antibody also has a higher binding affinity to BTLA as compared to HVEM binding BTLA. This may provide a benefit for patients having disease states with transient levels of HVEM, wherein it may be desirable to have a BTLA-mimicking agonist antibody on-board during times when the patient has a reduction in HVEM.

The present inventions provide antibodies that bind to BTLA and activate and/or enhance BTLA-mediated signaling (BTLA agonist antibodies). The present inventions provide an antibody that comprises a light chain variable region (LCVR) and a heavy chain variable region (HCVR), wherein the LCVR comprises complementarity determining regions (CDRs) LCDR1, LCDR2, and LCDR3 and the HCVR comprises CDRs HCDR1, HCDR2, and HCDR3, and wherein the amino acid sequence of LCDR1 is SEQ ID NO: 22, the amino acid sequence of LCDR2 is SEQ ID NO: 25, the amino acid sequence of LCDR3 is SEQ ID NO: 28, the amino acid sequence of HCDR1 is SEQ ID NO: 13, the amino acid sequence of HCDR2 is SEQ ID NO: 16, and the amino acid sequence of HCDR3 is SEQ ID NO: 19. In an embodiment, the antibody comprises a LCVR and a HCVR, and wherein the amino acid sequence of the LCVR is SEQ ID NO: 4, and the amino acid sequence of the HCVR is SEQ ID NO: 3. In another embodiment, the antibody comprises a light chain (LC) and a heavy chain (HC), and wherein the amino acid sequence of the LC is SEQ ID NO: 2, and the amino acid sequence of the HC is SEQ ID NO: 1. In yet another embodiment, the antibody comprises 2 LCs and 2 HCs, wherein the amino acid sequence of each LC is SEQ ID NO: 2, and the amino acid sequence of each HC is SEQ ID NO: 1.

The present inventions also provide a BTLA agonist antibody wherein the amino acid sequence of LCDR1 is SEQ ID NO: 23, the amino acid sequence of LCDR2 is SEQ ID NO: 26, the amino acid sequence of LCDR3 is SEQ ID NO: 29, the amino acid sequence of HCDR1 is SEQ ID NO: 14, the amino acid sequence of HCDR2 is SEQ ID NO: 17, and the amino acid sequence of HCDR3 is SEQ ID NO: 20. In an embodiment, the amino acid sequence of the LCVR is SEQ ID NO: 8, and the amino acid sequence of the HCVR is SEQ ID NO: 7. In another embodiment, the amino acid sequence of the LC is SEQ ID NO: 6, and the amino acid sequence of the HC is SEQ ID NO: 5. In yet another embodiment, the antibody comprises 2 LCs and 2 HCs, wherein the amino acid sequence of each LC is SEQ ID NO: 6, and the amino acid sequence of each HC is SEQ ID NO: 5.

The present inventions also provide a BTLA agonist antibody wherein the amino acid sequence of LCDR1 is SEQ ID NO: 24, the amino acid sequence of LCDR2 is SEQ ID NO: 27, the amino acid sequence of LCDR3 is SEQ ID NO: 30, the amino acid sequence of HCDR1 is SEQ ID NO: 15, the amino acid sequence of HCDR2 is SEQ ID NO: 18, and the amino acid sequence of HCDR3 is SEQ ID NO: 21. In an embodiment, the amino acid sequence of the LCVR is SEQ ID NO: 12, and the amino acid sequence of the HCVR is SEQ ID NO: 11. In another embodiment, the amino acid sequence of the LC is SEQ ID NO: 10, and the amino acid sequence of the HC is SEQ ID NO: 9. In yet another embodiment, the antibody comprises 2 LCs and 2 HCs, wherein the amino acid sequence of each LC is SEQ ID NO: 10, and the amino acid sequence of each HC is SEQ ID NO: 9.

The present invention also provides an antibody that binds BTLA, wherein the antibody is generated by steps comprising immunizing rabbits with Fc-tagged extracellular domain (ECD) domain of human BTLA and boosting with human and mouse BTLA-Fc tagged proteins. The amino acid sequence of the human BTLA ECD is amino acids 31-150 of SEQ ID NO: 31.

The present invention provides a BTLA agonist antibody that mimics HVEM binding to BTLA. The present invention also provides a BTLA agonist antibody that is able to bind human, cynomulgus monkey, and murine BTLA.

The present invention also provides a pharmaceutical composition comprising an antibody of the present invention, and one or more pharmaceutically acceptable carriers, diluents, or excipients. In some embodiments, pharmaceutical compositions of the present invention can be used in the treatment of one or more of rheumatic, neural, and dermatology disease, whereby such treatment comprises administering to a patient in need thereof an effective amount of a pharmaceutical composition of the present invention. In some particular embodiments, the rheumatic disease is at least one of lupus nephritis, systemic lupus erythematosus, and rheumatoid arthritis. In other particular embodiments, the dermatology disease is at least one of atopic dermatitis and psoriasis. In other particular embodiments, the neural disease is multiple sclerosis.

The present invention also provides a method of treating a patient having one or more of rheumatic, neural, and dermatology disease, comprising administering to a patient in need thereof an effective amount of an antibody of the present invention. In some such embodiments, the rheumatic disease is at least one of lupus nephritis, systemic lupus erythematosus, and rheumatoid arthritis. In other particular embodiments, the dermatology disease is at least one of atopic dermatitis and psoriasis. In other particular embodiments, the neural disease is multiple sclerosis.

The present invention also provides an antibody of the present invention or pharmaceutical composition thereof for use in therapy. In some embodiments, the present invention provides an antibody of the present invention or pharmaceutical composition thereof for use in the treatment of one or more rheumatic, neural, and dermatology disease. In some such embodiments, the rheumatic disease is at least one of lupus nephritis, systemic lupus erythematosus, and rheumatoid arthritis. In other particular embodiments, the dermatology disease is at least one of atopic dermatitis and psoriasis. In other particular embodiments, the neural disease is multiple sclerosis.

The present invention also provides the use of an antibody of the present invention or a pharmaceutical composition thereof in the manufacture of a medicament for the treatment of one or more of rheumatic, neural, and dermatology disease. In some such embodiments, the rheumatic disease is at least one of lupus nephritis, systemic lupus erythematosus, and rheumatoid arthritis. In other particular embodiments, the dermatology disease is at least one of atopic dermatitis and psoriasis. In other particular embodiments, the neural disease is multiple sclerosis.

The present invention provides a DNA molecule comprising a polynucleotide sequence encoding a polypeptide having the amino acid sequence of SEQ ID NO:1, SEQ ID NO:5, or SEQ ID NO:9. The present invention also provides a DNA molecule comprising a polynucleotide sequence encoding a polypeptide having the amino acid sequence of SEQ ID NO:2, SEQ ID NO:6, or SEQ ID NO:10.

The present invention provides a DNA molecule comprising a polynucleotide sequence encoding a polypeptide having the amino acid sequence of SEQ ID NO: 1, and comprising a polynucleotide sequence encoding a polypeptide having the amino acid sequence of SEQ ID NO: 2. The present invention also provides a DNA molecule comprising a polynucleotide sequence encoding a polypeptide having the amino acid sequence of SEQ ID NO: 1, and a DNA molecule comprising a polynucleotide sequence encoding a polypeptide having the amino acid sequence of SEQ ID NO: 2. In a particular embodiment the polynucleotide sequence encoding a polypeptide having the amino acid sequence of SEQ ID NO: 1 is SEQ ID NO: 35 and the polynucleotide sequence encoding a polypeptide having the amino acid sequence of SEQ ID NO: 2 is SEQ ID NO: 36.

The present invention also provides a DNA molecule comprising a polynucleotide sequence encoding a polypeptide having the amino acid sequence of SEQ ID NO: 5, and comprising a polynucleotide sequence encoding a polypeptide having the amino acid sequence of SEQ ID NO: 6. The present invention also provides a DNA molecule comprising a polynucleotide sequence encoding a polypeptide having the amino acid sequence of SEQ ID NO: 5, and a DNA molecule comprising a polynucleotide sequence encoding a polypeptide having the amino acid sequence of SEQ ID NO: 6. In a particular embodiment the polynucleotide sequence encoding a polypeptide having the amino acid sequence of SEQ ID NO: 5 is SEQ ID NO: 37, the polynucleotide sequence encoding a polypeptide having the amino acid sequence of SEQ ID NO: 6 is SEQ ID NO: 38.

The present invention also provides a DNA molecule comprising a polynucleotide sequence encoding a polypeptide having the amino acid sequence of SEQ ID NO: 9, and comprising a polynucleotide sequence encoding a polypeptide having the amino acid sequence of SEQ ID NO: 10. The present invention also provides a DNA molecule comprising a polynucleotide sequence encoding a polypeptide having the amino acid sequence of SEQ ID NO: 9, and a DNA molecule comprising a polynucleotide sequence encoding a polypeptide having the amino acid sequence of SEQ ID NO: 10. In a particular embodiment the polynucleotide sequence encoding a polypeptide having the amino acid sequence of SEQ ID NO: 9 is SEQ ID NO: 39, the polynucleotide sequence encoding a polypeptide having the amino acid sequence of SEQ ID NO: 10 is SEQ ID NO: 40.

Further, the present invention provides a mammalian cell comprising a DNA molecule comprising a polynucleotide sequence encoding a polypeptide having the amino acid sequence of SEQ ID NO: 1 and a DNA molecule comprising a polynucleotide sequence encoding a polypeptide having the amino acid sequence of SEQ ID NO: 2. The present invention also provides a mammalian cell comprising a DNA molecule comprising a polynucleotide sequence encoding a polypeptide having the amino acid sequence of SEQ ID NO: 5 and a polypeptide having the amino acid sequence of SEQ ID NO: 6. The present invention also provides a mammalian cell comprising a DNA molecule comprising a polynucleotide sequence encoding a polypeptide having the amino acid sequence of SEQ ID NO: 9 and a polypeptide having the amino acid sequence of SEQ ID NO: 10. In an embodiment the mammalian cell line is a Chinese Hamster Ovary (CHO) or Hamster embryonic kidney (HEK) cell line.

The present invention also provides a mammalian cell comprising a DNA molecule comprising a polynucleotide sequence encoding a polypeptide having the amino acid sequence of SEQ ID NO:1 and/or a DNA molecule comprising a polynucleotide sequence encoding a polypeptide having the amino acid sequence of SEQ ID NO: 2, wherein the cell is capable of expressing an antibody comprising a HC having the amino acid sequence of SEQ ID NO:1 and a LC having the amino acid sequence of SEQ ID NO: 2. Preferably the mammalian cell comprises a DNA molecule comprising a polynucleotide sequence encoding a polypeptide having the amino acid sequence of SEQ ID NO:1 and a polypeptide having the amino acid sequence SEQ ID NO: 2. In an embodiment the mammalian cell line is a CHO or HEK cell line.

The present invention also provides a mammalian cell comprising a DNA molecule comprising a polynucleotide sequence encoding a polypeptide having the amino acid sequence of SEQ ID NO:5 and/or a DNA molecule comprising a polynucleotide sequence encoding a polypeptide having the amino acid sequence of SEQ ID NO: 6, wherein the cell is capable of expressing an antibody comprising a HC having the amino acid sequence of SEQ ID NO:5 and a LC having the amino acid sequence of SEQ ID NO: 6. Preferably the mammalian cell comprises a DNA molecule comprising a polynucleotide sequence encoding a polypeptide having the amino acid sequence of SEQ ID NO:5 and a polypeptide having the amino acid sequence SEQ ID NO: 6. In an embodiment the mammalian cell line is a CHO or HEK cell line.

The present invention also provides a mammalian cell comprising a DNA molecule comprising a polynucleotide sequence encoding a polypeptide having the amino acid sequence of SEQ ID NO:9 and/or a DNA molecule comprising a polynucleotide sequence encoding a polypeptide having the amino acid sequence of SEQ ID NO: 10, wherein the cell is capable of expressing an antibody comprising a HC having the amino acid sequence of SEQ ID NO:9 and a LC having the amino acid sequence of SEQ ID NO: 10. Preferably the mammalian cell comprises a DNA molecule comprising a polynucleotide sequence encoding a polypeptide having the amino acid sequence of SEQ ID NO:9 and a polypeptide having the amino acid sequence SEQ ID NO: 10. In an embodiment the mammalian cell line is a CHO or HEK cell line.

In another embodiment, the present invention provides a process for producing an antibody comprising a LC having an amino acid sequence of SEQ ID NO: 2 and a HC having an amino acid sequence of SEQ ID NO: 1, wherein the process comprises cultivating a mammalian cell comprising a DNA encoding a LC having an amino acid sequence of SEQ ID NO: 2 and/or a HC having an amino acid sequence of SEQ ID NO: 1 under conditions such that the antibody is expressed, and recovering the expressed antibody. The invention includes an antibody obtainable by the process of the invention as described immediately above.

The present invention also provides a process for producing an antibody comprising a LC having an amino acid sequence of SEQ ID NO: 6 and a HC having an amino acid sequence of SEQ ID NO: 5, wherein the process comprises cultivating a mammalian cell comprising a DNA encoding a LC having an amino acid sequence of SEQ ID NO: 6 and/or a HC having an amino acid sequence of SEQ ID NO: 5 under conditions such that the antibody is expressed, and recovering the expressed antibody. The invention includes an antibody obtainable by the process of the invention as described immediately above.

The present invention also provides a process for producing an antibody comprising a LC having an amino acid sequence of SEQ ID NO: 10 and a HC having an amino acid sequence of SEQ ID NO: 9, wherein the process comprises cultivating a mammalian cell comprising a DNA encoding a LC having an amino acid sequence of SEQ ID NO: 10 and/or a HC having an amino acid sequence of SEQ ID NO: 9 under conditions such that the antibody is expressed, and recovering the expressed antibody. The invention includes an antibody obtainable by the process of the invention as described immediately above.

The present invention includes a process for producing an antibody, which antibody comprises two HCs and two LCs, in which the amino sequence of each of the two HCs is SEQ ID NO: 1, and the amino acid sequence of each of the two LCs is SEQ ID NO: 2, and which process comprises: a) cultivating a mammalian cell of the invention, as described above, under conditions such that the antibody is expressed, and b) recovering the expressed antibody. The invention includes an antibody obtainable by the process of the invention as described immediately above.

The present invention also includes a process for producing an antibody, which antibody comprises two HCs and two LCs, in which the amino sequence of each of the two HCs is SEQ ID NO: 5 and the amino acid sequence of each of the two LCs is SEQ ID NO: 6, and which process comprises: a) cultivating a mammalian cell of the invention, as described above, under conditions such that the antibody is expressed, and b) recovering the expressed antibody. The invention includes an antibody obtainable by the process of the invention as described immediately above.

The present invention also includes a process for producing an antibody, which antibody comprises two HCs and two LCs, in which the amino sequence of each of the two HCs is SEQ ID NO: 9 and the amino acid sequence of each of the two LCs is SEQ ID NO: 10, and which process comprises: a) cultivating a mammalian cell of the invention, as described above, under conditions such that the antibody is expressed, and b) recovering the expressed antibody. The invention includes an antibody obtainable by the process of the invention as described immediately above.

The present invention provides an antibody that contacts human BTLA at a structural and functional epitope having the following residues of SEQ ID NO: 31: Arg at position 42 and His at position 127. The present invention also provides an antibody that contacts human BTLA at a structural and functional epitope comprising Arg at position 42 of the amino acid sequence given by SEQ ID NO: 31.

The present invention provides an antibody that contacts human BTLA at a novel structural epitope having the following residues of SEQ ID NO: 31: Asp at position 35, Gln at position 37, Arg at position 42, Leu at position 74, Gly at position 76, Cys at position 79, Arg at position 114, Phe at position 119, Gln at position 120, Asn at position 122, Ser at position 128. In a preferred embodiment, the antibody 22B3 is said to mimic HVEM binding to BTLA because the HCDR3 of antibody 22B3 is structurally similar to HVEM. Preferably, when the BTLA:antibody crystal structure is aligned with the BTLA:HVEM crystal structure in a program such as PyMOL™, an antibody CDR loop adopts a conformation similar to the HVEM loop comprising amino acid residues 69 to 72 (amino acids ELTG of SEQ ID NO:41).

The present invention provides an antibody that contacts human BTLA at a functional epitope having Asp at position 52 of SEQ ID NO:31. The antibody contacts a novel structural epitope having the following residues of SEQ ID NO: 31: His at position 46, Glu at position 55, Glu at position 103, Pro at position 104, Leu at position 106, Pro at position 107, Thr at position 134, Ala at position 139.

The present invention provides an antibody that contacts human BTLA at a functional epitope having His at position 68 and Lys at position 81 of SEQ ID NO:31. In an embodiment, the antibody contacts a novel structural epitope having the following residues of SEQ ID NO: 31: Tyr at position 62, Ala at position 64, His at position 68, Arg at position 85, Glu at position 91, Phe at position 98, Asn at position 118.

The present invention provides an antibody that contacts human BTLA at a novel structural epitope having the following residues of SEQ ID NO: 31: Asp at position 35, Gln at position 37, Arg at position 42, Leu at position 74, Gly at position 76, Cys at position 79, Arg at position 114, Phe at position 119, Gln at position 120, Asn at position 122, and Ile at position 124, Ser at position 128.

As used herein, an "antibody" is an immunoglobulin molecule comprising 2 HCs and 2 LCs interconnected by disulfide bonds. The amino terminal portion of each LC and HC includes a variable region of about 100-120 amino acids primarily responsible for antigen recognition via the CDRs contained therein. The CDRs are interspersed with regions that are more conserved, termed framework regions ("FR"). Each LCVR and HCVR is composed of 3 CDRs and 4 FRs, arranged from amino-terminus to carboxy-terminus in the following order: FR1, CDR1, FR2, CDR2, FR3, CDR3, FR4. The 3 CDRs of the LC are referred to as "LCDR1, LCDR2, and LCDR3," and the 3 CDRs of the HC are referred to as "HCDR1, HCDR2, and HCDR3." The CDRs contain most of the residues which form specific interactions with the antigen. That is, the CDRs contain most of the residues that are in contact with (within 4.5 Å) the antigen's residues. The functional ability of an antibody to bind a particular antigen is, thus, largely influenced by the amino acid residues within the six CDRs. Assignment of amino acids to CDR domains within the LCVR and HCVR regions of the antibodies of the present invention is based on the well-known Kabat numbering convention (Kabat, et al., Ann. NY Acad. Sci. 190:382-93 (1971); Kabat et al., Sequences of Proteins of Immunological Interest, Fifth Edition, U.S. Department of Health and Human Services, NIH Publication No. 91-3242 (1991)), and Chothia (Chothia C, Lesk A M. Canonical structures for the hypervariable regions of immunoglobulins. J. Mol. Biol. 1987; 196:901-17. Chothia C, Lesk A M, Tramontano A, Levitt M, Smith-Gill S J, Air G, Sheriff S, Padlan E A, Davies D, Tulip W R, et al. Conformations of immunoglobulin hypervariable regions. Nature. 1989; 342:877-83). The starting amino acid residue of HCDR1 is defined by Chothia and the ending amino acid reside for HCDR1 is defined by Kabat. The starting and ending amino acid residues for HCDR2, HCDR3, LCDR1, LCDR2, and LCDR3 are defined by Kabat.

The term "epitope" as used herein may refer to a structural epitope (sites of an antigen that are in contact with the variable region of an antibody) and/or a functional epitope (sites of an antigen that may or may not be in contact with the variable region of an antibody and are necessary for antibody binding). The structural epitope is determined by X-ray crystallography wherein any residue on human BTLA within 4.5A of another residue on the bound Fab is considered to be a contact site.

The antibodies of the present invention may be prepared and purified using known methods. For example, cDNA sequences encoding a HC (for example the amino acid sequence given by SEQ ID NO: 1) and a LC (for example, the amino acid sequence given by SEQ ID NO: 2) may be cloned and engineered into a GS (glutamine synthetase) expression vector. The engineered immunoglobulin expression vector may then be stably transfected into CHO cells. As one skilled in the art will appreciate, mammalian expression of antibodies will result in glycosylation, typically at highly conserved N-glycosylation sites in the Fc region. Stable clones may be verified for expression of an antibody specifically binding to BTLA. Positive clones may be expanded into serum-free culture medium for antibody production in bioreactors. Medium, into which an antibody has been secreted, may be purified by conventional techniques. For example, the medium may be conveniently applied to a Protein A or G Sepharose FF column that has been equilibrated with a compatible buffer, such as phosphate buffered saline. The column is washed to remove nonspecific binding components. The bound antibody is eluted, for example, by pH gradient and antibody fractions are detected, such as by SDS-PAGE, and then pooled. The antibody may be concentrated and/or sterile filtered using common techniques. Soluble aggregate and multimers may be effectively removed by common techniques, including size exclusion, hydrophobic interaction, ion exchange, or hydroxyapatite chromatography. The product may be immediately frozen, for example at −70° C., or may be lyophilized.

An antibody of the present invention can be incorporated into a pharmaceutical composition which can be prepared by methods well known in the art and comprise an antibody of the present invention and one or more pharmaceutically acceptable carriers, diluents, or excipients.

A pharmaceutical composition comprising an effective amount of an antibody of the present invention can be administered to a patient at risk for, or exhibiting, diseases or disorders as described herein by parental routes (e.g., subcutaneous, intravenous, intraperitoneal, intramuscular, or transdermal). An "effective amount" refers to an amount necessary (at dosages and for periods of time and for the means of administration) to achieve the desired therapeutic result. An effective amount of the antibody may vary according to factors such as the disease state, age, sex, and weight of the individual, and the ability of the antibody to elicit a desired response in the individual. An effective amount is also one in which any toxic or detrimental effects of the antibody of the present invention are outweighed by the therapeutically beneficial effects.

The antibodies of the present invention can be used in the treatment of patients. More particularly the antibodies of the present invention are expected to treat one or more of rheumatic, neural, and dermatology disease. Rheumatic diseases are characterized by inflammation that can affect a person's joints, muscles, and/or organs. One such rheumatic disease is systemic lupus erythematosus (SLE).

As used interchangeably herein, "treatment" and/or "treating" and/or "treat" are intended to refer to all processes wherein there may be a slowing, interrupting, arresting, controlling, stopping, or reversing of the progression of the disorders described herein, but does not necessarily indicate a total elimination of all disorder symptoms. Treatment includes administration of an antibody of the present invention for treatment of a disease or condition in a human that would benefit from an increase in BTLA activity, and includes: (a) inhibiting further progression of the disease; and (b) relieving the disease, i.e., causing regression of the disease or disorder or alleviating symptoms or complications thereof.

Antibody Engineering

The antibodies of the present invention were generated by immunizing rabbits with Fc-tagged extracellular domain (ECD) domain of human BTLA and boosting with mouse BTLA-Fc tagged protein (25F7) or alternately with human and mouse BTLA-Fc tagged proteins (22B3 and 23C8). Screening was done with histidine-tagged human, mouse, and cynomolgus monkey BTLA to identify cross reactivity. The amino acid sequence of human BTLA is given by SEQ ID NO: 31, the amino acid sequence of Balbc mouse BTLA is given by SEQ ID NO: 32, the amino acid sequence of C57BL6 is given by SEQ ID NO:33, and the amino acid sequence of cynomolgus monkey BTLA is given by SEQ ID NO: 34. The antibodies were then humanized and affinity matured.

EXAMPLES

Expression and Purification of Engineered BTLA Agonist Antibodies

BTLA agonist antibodies of the present invention can be expressed and purified essentially as follows. An appropriate host cell, such as HEK 293 or CHO, can be either transiently or stably transfected with an expression system for secreting antibodies using an optimal predetermined HC:LC vector ratio (such as 1:3 or 1:2) or a single vector system encoding both the HC and the LC. Clarified media, into which the antibody has been secreted, may be purified using any of many commonly-used techniques. For example, the medium may be conveniently applied to a Mab Select column (GE Healthcare), or KappaSelect column (GE Healthcare) for Fab fragment, that has been equilibrated with a compatible buffer, such as phosphate buffered saline (pH 7.4). The column may be washed to remove nonspecific binding components. The bound antibody may be eluted, for example, by pH gradient (such as 20 mM Tris buffer, pH 7.0 to 10 mM sodium citrate buffer, pH 3.0, or phosphate buffered saline pH 7.4 to 100 mM glycine buffer, pH 3.0). Antibody fractions may be detected, such as by SDS-PAGE, and then may be pooled. Further purification is optional, depending on intended use. The antibody may be concentrated and or sterile filtered using common techniques. Soluble aggregate and multimers may be effectively removed by common techniques, including size exclusion, hydrophobic interaction, ion exchange, multimodal, or hydroxyapatite chromatography. The purity of the antibody after these chromatography steps is between about 95% to about 99%. The product may be held refrigerated, immediately frozen at −70° C., or may be lyophilized. Amino acid SEQ ID NOs for exemplified antibodies of the present invention are shown below.

TABLE 1

Amino acid sequences of exemplified BTLA agonist antibodies. Antibody SEQ ID NOs

| Antibody | HCDR1 | HCDR2 | HCDR3 | LCDR1 | LCDR2 | LCDR3 |
|---|---|---|---|---|---|---|
| 22B3 | 13 | 16 | 19 | 22 | 25 | 28 |
| 23C8 | 14 | 17 | 20 | 23 | 26 | 29 |
| 25F7 | 15 | 18 | 21 | 24 | 27 | 30 |

Binding Affinity and Kinetics

The binding affinity and kinetics of the BTLA agonist antibodies of the present invention (22B3, 23C8, and 25F7) to BTLA are measured by surface plasmon resonance using Biacore® 3000 (GE Healthcare). The binding affinity is measured by immobilizing about 120 RU BTLA protein (human, rat, murine (Balbc or C57BL6), or cynomolgus monkey BTLA) via amine coupling on a Biacore® CM5 chip, and flowing BTLA agonist antibody, starting from 500 nM in 2-fold serial dilution down to 15.6 nM. The experiments are carried out at 25° C. in HBS-EP buffer (GE Healthcare BR100669; 10 mM HEPES, 150 mM NaCl, 3 mM EDTA, 0.05% surfactant P20, pH 7.4). For each cycle, 250 µL antibody sample is flowed through flow cell 1 and 2 at 50 µl/min, and then dissociated for 10 minutes. The chip surface is regenerated with 5 µL injection of glycine buffer at pH 1.5 at 10 µL/mL flow rate. The data are fit to a 1:1 Langmuir binding model to derive $k_{on}$, $k_{off}$, and to calculate $K_D$. Following procedures essentially as described above, the following parameters (shown in Table 2) were observed. Data shown below are the average of three experiments for human, cyno, rat and murine for 22B3.

TABLE 2

Binding affinity and kinetics.

| Antibody | Antigen (BTLA) | $k_{on}$ (1/Ms) | $k_{off}$ (1/s) | $K_D$ (nM) |
|---|---|---|---|---|
| 22B3 | Human | 5.87E+06 | 2.19E−03 | 0.365 |
| | Cyno | 2.45E+06 | 6.47E−04 | 0.27 |
| | Murine (balbc) | 2.60E+06 | 8.58E−02 | 32.5 |
| | Murine (C57BL6) | 1.89E+06 | 2.65E−01 | 147 |
| | Rat | 2.10E+06 | 4.62E−02 | 24.1 |
| 23C8 | Human | 1.59E+05 | 2.93E−04 | 1.93 (n = 3) |
| | Cyno | 8.71E+04 | 3.09E−03 | 35.35 (n = 2) |
| | Murine (balbc) | No Binding | No Binding | No Binding |
| | Murine (C57BL6) | No Binding | No Binding | No Binding |
| | Rat | Not Tested | Not Tested | Not Tested |
| 25F7 | Human | 6.8622E+04 | 1.42E−02 | 206.2 (n = 2) |
| | Cyno | Not Tested | Not Tested | Not Tested |
| | Murine (balbc) | Not Tested | Not Tested | Not Tested |
| | Murine (C57BL6) | 7.70E+04 | 3.50E−04 | 4.63 (n = 1) |
| | Rat | Not Tested | Not Tested | Not Tested |

As shown above in Table 2, the BTLA agonist antibodies of the present invention bind BTLA. Specifically, antibody 22B3 is able to bind human, murine, and cynomolgus monkey BTLA.

Binding to Primary Cells

The ability of BTLA antibodies of the present invention (22B3, 23C8, and 25F7) to bind primary cells from different species is determined by FACS. Human peripheral blood mononuclear cells (PBMCs) are isolated from a donor blood sample (San Diego Blood Bank, # LRS-WBC) using Ficoll (GE #17-1440-02) and SepMate tubes (STEMCELL #15450), per manufacturer's protocol. Cyno PBMCs (WorldWide Primates # CA-10) are thawed from liquid nitrogen and washed once with FACS buffer (same as above).

Spleens from male C57BL6 mice (JAX) or female Sprague Dawley rats (Harlan) are harvested, pooled, and dissociated into single cell suspensions using a cell strainer and syringe plunger over a 50 mL conical tube rinsed with RPMI 1640 complete with 10% heat inactivated FBS and 2 mM EDTA. Cells are pelleted, media removed, and red blood cells lysed by resuspending pellet in 2 ml ACK Lysing Buffer (gibco # A10492-01) for approximately 2 minutes before quenching with complete RPMI. Lysed cells may be pelleted and washed once in FACS buffer (DPBS 1× containing 3% FBS, 20 mM HEPES, and 2 mM EDTA).

Isolated primary cells are quantified using a Countess cell counter, and resuspended at $2\times10^6$ cells per ml in FACS buffer. Flow cytometry experiments is performed the same day as cell isolation by plating 50 µl (~$0.1\times10^6$) cells into a 96 well plate (Greiner #650101). Non-specific antibody binding is prevented by adding 1 µl Fc block (for example, from BD #553142) for 15 minutes at 4° C. without washing.

BTLA antibody binding is tested at various concentrations, by serial dilution in FACS buffer. For example, a purified antibody and controls starting at different concentrations are first diluted to 30 µg/mL and serial 1:3 dilutions of the starting material is performed for a total of 10 titrations (plus untreated control). Antibody titrations are incubated with cells for 20 minutes at 4° C., and washed with FACS buffer prior to stain. Cells are stained using fluorochrome-conjugated antibodies to identify specific cell types (eg. CD19 B cells, CD4 T cells or CD8 T cells) or using a secondary antibody to identify the presence or absence of antibody binding to that subset. Staining is performed for 20 minutes at 4° C. and washed 3 times with FACS buffer prior to analysis on a flow cytometer. Results are analyzed using standard FACS analysis software (eg. FACSDiva) and reported as mean fluorescent intensity of the secondary antibody for each titration. A positive result, which indicates binding, is determined by mean fluorescent intensity staining above background.

Following procedures essentially as described above, antibody 22B3 binds to human, cynomolgus monkey, rat, and mouse BTLA-expressing cells, antibody 23C8 binds human and cynomolgus monkey BTLA-expressing cells, and antibody 25F7 binds human, cynomolgus monkey, and mouse BTLA-expressing cells.

BTLA Agonist Antibody-Induced Phosphorylation

To determine the ability of BTLA agonist antibodies of the present invention (22B3 and 25F7) to induce tyrosine phosphorylation in a human B cell line, a BTLA antibody is bound to a 24-well culture plate at 10 µg/mL for one hour at 37° C. hour. The plate is washed with PBS to remove any unbound antibody. A human BTLA-expressing B cell line, such as Ramos.2G6.4C10 human B Lymphocyte cell line (ATCC), may be added to the wells at $10\times10^6$ cells/mL and incubated for 37° C. for 30 min. The cells are removed and lysed in Complete Lysis Buffer (MSD), and frozen at −80° C. for at least 30 min.

Phosphorylated-BTLA is detected by Meso Sector S 600. Streptavidin detection plates are prepared by incubating in blocking solution (MSD) for one hour at room temperature. A biotinylated-BTLA capture antibody (5A5) is coated onto the plate for one hour at room temperature followed by three or more Tris-wash steps. The cell lysates are incubated for two hours at room temperature. Total BTLA is detected with a SULFO-TAG anti-BTLA antibody (ANC6E9) and phosphorylated BTLA is measured with a SULFO-TAG anti-phosphotryosine antibody (PY20; MSD) followed by three or more Tris-wash steps. Addition of 2× Read Buffer T (MSD) is then added to the wells immediately prior to analysis using a Meso Sector S 600.

Following procedures essentially as described above, antibody 22B3 resulted in a 2.41-fold increase in tyrosine phosphorylation of BTLA over background compared to negative control, and antibody 25F7 resulted in a 1.47-fold increase in tyrosine phosphorylation of BTLA over background compared to negative control. These data demonstrate that the BTLA agonist antibodies 22B3 and 25F7 are able to induce BTLA phosphorylation in a human B cell line.

Inhibition of Human Primary B Cell Proliferation

The in vitro potency of BTLA agonist antibodies of the present invention are evaluated by the ability to inhibit human primary B cell proliferation. Human primary B cells are isolated from healthy human peripheral blood mononuclear cells using human B cell isolation kit (EasySep) and are resuspended in appropriate human primary cell media. Anti-IgM is coated to plates along with titrations of isotype control or BTLA antibody and incubated for one hour at 37° C. followed by PBS wash step. Isolated human B cells are added to each well and incubated for 72 hours at 37° C. with 5% CO2 followed by [$^3$H]-thymidine pulse for the last 18 hours. Post incubation plates are removed and placed on dry ice for 30 minutes and then stored at −20° C. until ready to harvest. Cells are lysed by thawing and harvested with Harvester9600 (Tomtec). Proliferation is assessed by measuring [$^3$H]-thymidine incorporation with a MicroBeta$^2$ 2450 Microplate Counter (Perkin Elmer).

Counts are used to assess relative proliferative response in this assay, and percent inhibition is calculated using the equation [% Inhibition=(AVGmaxsignal−signalsample)/AVGmaxsignal×100], which can be used to determine $IC_{50}$ values using graphing software (GraphPad Prism).

Following procedures essentially as described above, the BTLA agonist antibody 22B3 was able to inhibit primary B cell proliferation in vitro with a calculated $IC_{50}$ of 0.32+/−0.1 nM, antibody 23C8 was able to inhibit primary B cell proliferation in vitro with a calculated $IC_{50}$ of 0.14 nM, and antibody 25F7 was able to inhibit primary B cell proliferation in vitro with a calculated $IC_{50}$ of 0.17 nM. In a similar experiment, antibody 22B3 was able to inhibit primary B cell proliferation with a calculated $IC_{50}$ of 0.32 nM, and an antibody having the same HCVRs and LCVRs as Mab8D5 (SEQ ID NO: 11 and 18 of the '694 patent, respectively) inhibited primary B cell proliferation with a calculated $IC_{50}$ of 6.38 nM. These data demonstrate that the BTLA agonist antibodies 22B3, 23C8, and 25F7 are able to inhibit B cell proliferation in vitro, and that antibody 22B3 has greater in vitro activity as compared to Mab8D5.

Humanized NSG Mouse Model of GvHD

Prevention of human PBMC-driven graft vs. host disease (GvHD) is determined in vivo.

Briefly, female NSG mice (JAX Labs, Stock #05557), approximately 8-10 weeks old, are normalized and divided into treatment groups (n=8 mice per treatment group) based on baseline body weight measurements. Peripheral blood mononuclear cells (PBMCs) are isolated from a blood donor program (San Diego Blood Bank, # LRS-WBC) using Ficoll (GE #17-1440-02) and SepMate tubes (STEMCELL #15450), per manufacturer's protocol. PBMCs are resuspended at approximately 150×106 cells per ml of PBS. Treatment groups are blinded prior to dosing.

On day 1, 100 µl (15×106 cells) of PBMCs suspended in PBS (as described above) (or 100 µl PBS for non-engrafted controls) are injected intravenously (IV) into the tail of each mouse. Mice are dosed weekly (QW) with antibody of the present invention (22B3 or 23C8) or controls at varying concentrations in PBS vehicle, by subcutaneous (SQ) injections. Three independent studies are performed essentially as described herein. Dosing concentrations for each study is [Study 1 (antibody 22B3): 0.1, 1.0, 5.0, 10.0, and 20.0 mg/kg; Study 2 (antibody 22B3 or 23C8): 0.001, 0.01, 10.0, and 100 mpk; and Study 3: 0.001, 0.005, 0.01, 0.1, 0.5, and 1.0 mpk].

The study is terminated and mice are euthanized prior to isotype control animals losing 20% loss of baseline body weight (Studies 1 and 2) or day 28 (Study 3). Weights are recorded (Study 1 and Study 2), serum is collected for cytokine analysis (Study 1; analysis is performed by MSD ELISA; cytokines analyzed are TNFα, IL-10, IL-6, IL-4, IL12p70, IL-13, IL-2, and IL-8), and spleens are harvested for phenotyping/pharmacodynamic analyses (measured by a reduction in CD 8 T cell population; Study 1 and Study 3).

Following procedures essentially as described above, the following data were obtained.

Antibody 22B3-treated animals in Study 1 demonstrated the following (at doses 0.1, 1.0, 5.0, 10.0, or 20.0 mg/kg antibody): (i) similar body weights at the end of the study compared to the body weights of non-engrafted control animals; (ii) a reduction in the cytokines TNFα, IL-10, IL-6, IL-4, and IL-12p70 compared to isotype control animals; and (iii) a reduction in CD 8 T cell population compared to isotype control animals (phenotyping/pharmacodynamic analyses).

Data from Study 2 demonstrate that mice treated with 0.01 mg/kg antibody 22B3, or 1.0, 5.0, or 10.0 mg/kg antibody 23C8 had similar body weights at the end of the study compared to the body weights of non-engrafted control animals. Study 2 did not demonstrate activity of 22B3 on body weight at 10.0 mg/kg, which may reflect natural donor variability of this model. In Study 3, antibody 22B3 demonstrated pharmacodynamic activity in vivo at the following doses of antibody: 0.01, 0.1, 0.5, and 1.0 mg/kg. Taken together, these data demonstrate that antibody 22B3 and antibody 23C8 were efficacious in preventing GvHD in vivo.

mIFNα-Induced Lupus Nephritis

The interferon-alpha (IFNα)-induced lupus nephritis model is a mouse model of systemic lupus erythematosus (SLE) in which IFNα is used to synchronize onset and accelerate progression of disease in a cross with New Zealand Black and New Zealand White (NZB/W) mice. The NZB/W mouse model is a classical model of spontaneous lupus nephritis. The disease progression in these mice could be accelerated with exogenous administration of IFNα using adenovirus vectors. This lupus nephritis model is used to demonstrate the activity of the BTLA agonist antibodies of the present invention.

One day before the study start, eleven week old female NZB/W mice are randomly sorted based on body weight. Mice are distributed into the following treatment groups: (1) LacZ adeno-associated virus (AAV+10 mg/kg human IgG4 PAA isotype control (PAA is S228P, F234A, and L235A mutations), (2) IFNα AAV+10 mg/kg human IgG4 PAA isotype control, (3) IFNα AAV+3 mg/kg 22B3 antibody, (4) IFNα AAV+10 mg/kg 22B3 antibody, or (5) IFNα AAV+50 mg/kg cyclophosphamide. On study start date (Day 0), mice are either administered once with $10^{11}$ genome copies (GC) of AAV expressing LacZ gene (non-diseased) or mouse IFNα (diseased) in PBS intravenously. In groups 1-4, the mice are treated with isotype control or 22B3 antibody antibodies in PBS subcutaneously once every week starting on Day 0. In group 5, mice are treated with cyclophosphamide in PBS intraperitoneally every 10 days. Urine samples are collected from the mice every 2 weeks until study termination 6 weeks after treatment initiation. The Kamiya Biomedical™ mouse microalbumin ELISA is used to quantitate urine albumin levels. Urine creatinine is measured by using an enzymatic creatinine assay (Roche Diagnostics). Albuminuria, a biomarker of renal function, is defined as greater than 300 µg albumin per mg creatinine detected in the urine.

Following procedures essentially as described above, by week 4, the incidence of albuminuria in the isotype treated diseased group (IFNα AAV+hIgG4 PAA) reached 100% and stayed elevated until end of study, while the LacZ AAV treated (non-diseased) mice did not show any incidence of albuminuria. Cyclophosphamide, which can be acutely nephrotoxic, caused a transient increase in albuminuria in diseased mice, but the incidence of albuminuria in the cyclophosphamide group was reduced to zero by study end. Antibody 22B3 at 3 mg/kg and 10 mg/kg was able to reduce incidence of albuminuria to 50% and 20%, respectively, at day 28, and 60% and 70%, respectively, at day 42. These results indicated that antibody 22B3 was able to preserve renal function in the model.

A Kaplan-Meier plot (data not shown) of percent survival during the study showed that renal insufficiency in the isotype treated diseased group led to deaths starting at day 28. By the end of the study, survival rate in the isotype treated diseased group was 60%. The non-diseased and cyclophosphamide treated groups had survival rates of 100%. The mice treated with 10 mg/kg antibody 22B3 also showed 100% survival at the end of the study, while the mice treated with 3 mg/kg showed 80% survival. These results indicated that antibody 22B3 was able to prevent disease related deaths in this model.

Imiquimod-Induced Model of Psoriasis

The ability of an antibody of the present invention to limit the severity of psoriasis-like dermatitis induced by application of the TLR7/8 agonist imiquimod (IMQ) is tested. Seven-week-old, female B6.SJL-Ptprc$^a$ Pepc$^b$/BoyJ mice (JAX stock number: 002014), or HVEM$^{-/-}$ mice (described in Wang et al, J. Clin. Invest., 115:3, 711-717, March 2005) are injected intraperitoneally with 3 mg/kg or 1 mg/kg of antibody 22B3 or antibody 25F7, respectively, on day 0, and the backs of the mice are shaved. Animals injected with hIgG4 isotype control served as controls. On days 1-3, mice are anesthetized with inhaled isoflurane (VetOne), and 5% IMQ cream (50 mg, Fougera) is then applied to a defined area of the shaved skin. On day 4, the treated area of skin is excised and analyzed for disease severity and inflammation-related gene expression.

Following procedures essentially as described above, histological analysis demonstrated thickening of the epidermal layer with parakeratosis and hyperkeratosis in the groups treated with hIgG4 isotype control or 1 mg/kg antibody 22B3. Mice treated with 3 mg/kg antibody 22B3 or 3 mg/kg antibody 25F7 showed a significant reduction in epidermal thickness, with some areas appearing histologically normal. Gene expression in the skin was analyzed by qPCR using the iTaq Universal SYBR Green Supermix (Bio-Rad). Mice treated with 3 mg/kg antibody 22B3 exhibited a significant decrease in expression of Type I IFNs (IFNα, IFNβ) and IFNγ, as well as IFN-response genes (Isg15, Mx1, Mx2, Oas2). Analysis of cytokines involved in establishing IMQ-induced dermatitis also demonstrated a significant reduction in IL-22 and IL-23 expression in the 3 mg/kg antibody 22B3 treatment group. These data demonstrate that the BTLA agonist antibodies 22B3 and 25F7 are able to reduce epidermal thickness in a mouse model of psoriasis-like dermatitis.

Epitope Determination

The functional epitopes of the BTLA agonist antibodies of the present invention are determined by ELISA, and the structural epitopes are determined by x-ray crystallography.

Methods

ELISA: Functional Epitope

The following set of surface mutations of BTLA were introduced individually into a human BTLA protein fused to (human) Fc: D35R, Q37R, Y39E, R42D, Q43A, E45R, S47H, L49R, D52R, E55R, E57R, D84R, N65R, H68A, V80R, K81E, E83R, S88H, K90H, E91H, I95R, E103H, L106R, N108R, R114V, S121Y, N122R, E125H, H127E, T130R, Y132R, and T134H.

Binding of 22B3 and 23C8 was determined using an ELISA wherein the antibody to be epitope mapped was captured by an immobilized anti-rabbit antibody and after washing each BTLA mutant was incubated as a 4 point 4-fold dilution series with the captured antibody and detected with an enzyme linked anti-human Fc reagent. The resulting signal was compared among antibodies and to control antibodies. The functional epitope normally indicated itself by a dramatic reduction in signal for one or two mutants. For the 25F7 antibody, a sandwich ELISA was performed, wherein humanized 22B3 was immobilized, BTLA mutants were captured, and bound by rabbit 25F7. This gave a much stronger signal and the 25F7 epitope could be identified after eliminating the 22B3 epitope.

X-Ray Crystallography: Structural Epitope

In order to determine interacting interfaces and therefore the physical epitope on BTLA of the various antibodies, human BTLA was co-crystallized with the Fab portion of an antibody of the present invention and a crystal structure was determined. From the resulting crystal structure, the BTLA residues within 4.5A of any antibody atom were counted as part of the epitope (using the Pymol visualization software). 4.5 angstroms is measured from atom center to atom center. Any residue with at least one atom that is 4.5 angstroms close to any atom in the antibody is part of the epitope.

Two 22B3 structures were determined in complex with human BTLA. The first utilized the parent rabbit 22B3 antibody Fab, Histidine tagged and purified with a S47H mutant (stabilizing mutation) of human BTLA expressed as an Fc fusion and then cleaved and purified. These two proteins were mixed at an approximately equimolar ratio and screened in commercially available screens for crystallization. Crystals were obtained and diffraction data collected at the Advanced Photon Source. This data was reduced and solved by molecular replacement and refined to yield a high resolution structure of the complex between 22B3 and BTLA. The second complex was between an affinity matured version (with HC mutations I56Q/T57H/G98A and LC S95H) of the humanized 22B3 (Fab portion) and human BTLA. These were co-expressed, purified as a complex and similarly screened. The resulting structure and epitope were similar to the first structure.

The structure of 23C8 in complex was obtained in the same way as the first 22B3 complex, namely by purifying the His tagged rabbit parent Fab, mixing with monomeric S47H human BTLA and crystallizing.

The structure of 25F7 in complex with human BTLA was obtained as per the second 22B3 complex, namely by co-expression, co-purification and crystallization. A double mutant of the humanized 25F7 with improved binding to human BTLA was utilized (humanized 25F7 used for epitope determination has mutations at HC S30W/LC E27R).

Results

22B3 antibody: Among a set of BTLA surface mutants, R42D and H127E had a significant negative impact on binding to rabbit 22B3 antibody (comprising the same CDRs as 22B3 but with a rabbit framework). The functional epitope comprises Arg at position 42 and His at position 127 of human BTLA (SEQ ID NO:31). BTLA residues that are within 4.5 angstroms of 22B3 in the crystal structure complex between human BTLA and rabbit 22B3 Fab, and are the structural epitope, are the following residues of SEQ ID NO: 31: Asp at position 35, Gln at position 37 to Arg at position 42, Leu at position 74, Gly at position 76 to Cys at position 79, Arg at position 114, Phe at position 119, Gln at position 120, and Asn at position 122 to Ser at position 128. BTLA residues that are within 4.5 angstroms of 22B3 in the crystal structure complex between human BTLA and a human 22B3 variant (HC I56Q/T57H/G98A LC S95H) Fab are Asp at position 35, Gln at position 37 to Arg at position 42, Leu at position 74, Gly at position 76 to Cys at position 79, Arg at position 114, Phe at position 119, Gln at position 120, Asn at position 122, and Ile at position 124 to Ser at position 128 of SEQ ID NO:31.

In a similar study, the structural epitope for HVEM binding BTLA was the following amino acids of BTLA: Gln at position 37 to Arg at position 42, Leu at position 74, Gly at position 76, Thr at position 77, Ser at position 112, Arg at position 114, Asn at position 118, Ser at position 121 to Ser at position 128, and Thr at position 130. Structural similarity between antibody 22B3 and HVEM was assessed by superimposing the antibody:BTLA crystal structure onto the HVEM:BTLA crystal structure aligning the BTLA molecules. The backbone root-mean-square deviation in the HVEM region containing amino acid residues 69-72 and the corresponding antibody region was determined to be 1.4 angstroms.

23C8 antibody: D52R blocks binding of rabbit 23C8 (comprising the same HCDR1, HCDR2, HCDR3, LCDR1 and LCDR2 as 23C8, having the LCDR3 of QCTYGGV-VGSTSDDNP, and having a rabbit framework) to human BTLA in an ELISA. The functional epitope comprises Asp at position 52 of human BTLA (SEQ ID NO:31). BTLA residues that are within 4.5 angstroms of 23C8 in the crystal structure complex between human BTLA (S47H) and rabbit 23C8 Fab, and are the structural epitope, are His at position 46 to Glu at position 55, Glu at position 103, Pro at position 104, Leu at position 106, Pro at position 107, Thr at position 134 to Ala at position 139 of SEQ ID NO:31. Antibody 23C8 does not mimic HVEM binding.

25F7 antibody: Among a set of BTLA surface mutants, H68A and K61E had a significant negative impact on binding to rabbit 25F7 antibody (comprising the same CDRs as 25F7 but with a rabbit framework). The functional epitope comprises His at position 68, and Lys at position 81, of human BTLA (SEQ ID NO:31). BTLA residues that are within 4.5 angstroms of 25F7 in the crystal structure complex between human BTLA and humanized 25F7 Fab variant (HC S30W, LC E27R), and are the structural epitope, are Tyr at position 62, Ala at position 64 to His at position 68, Arg at position 85 to Glu at position 91, Phe at position 98, and Asn at position 118 of SEQ ID NO:31. Antibody 25F7 does not mimic HVEM binding.

Sequences

HC of Antibody 22B3 (SEQ ID NO: 1)
QVQLVQSGAEVKKPGASVKVSCKASGFSLSSYGVSWVRQAPGQGLEWMGAISY
DGITYYASWAKSRVTMTRDTSTSTVYMELSSLRSEDTAVYYCARGDYYDDYVY
VYALDIWGQGTLVTVSSASTKGPSVFPLAPCSRSTSESTAALGCLVKDYFPEPVT
VSWNSGALTSGVHTFPAVLQSSGLYSLSSVVTVPSSSLGTKTYTCNVDHKPSNTK
VDKRVESKYGPPCPPCPAPEAAGGPSVFLFPPKPKDTLMISRTPEVTCVVVDVSQE
DPEVQFNWYVDGVEVHNAKTKPREEQFNSTYRVVSVLTVLHQDWLNGKEYKC
KVSNKGLPSSIEKTISKAKGQPREPQVYTLPPSQEEMTKNQVSLTCLVKGFYPSDI
AVEWESNGQPENNYKTTPPVLDSDGSFFLYSRLTVDKSRWQEGNVFSCSVMHEA
LHNHYTQKSLSLSLG LC of Antibody 22B3 (SEQ ID NO: 2)
EIVLTQSPGTLSLSPGERATLSCQASQSISTALAWYQQKPGQAPRLLIYAASTLAS
GIPDRFSGSGSGTDFTLTISRLEPEDFAVYYCQQGYSSSNLDNVFGGGTKVEIKRT
VAAPSVFIFPPSDEQLKSGTASVVCLLNNFYPREAKVQWKVDNALQSGNSQESVT
EQDSKDSTYSLSSTLTLSKADYEKHKVYACEVTHQGLSSPVTKSFNRGEC HCVR of Antibody 22B3 (SEQ ID NO: 3)
QVQLVQSGAEVKKPGASVKVSCKASGFSLSSYGVSWVRQAPGQGLEWMGAISY
DGITYYASWAKSRVTMTRDTSTSTVYMELSSLRSEDTAVYYCARGDYYDDYVY
VYALDIWGQGTLVTVSS LCVR of Antibody 22B3 (SEQ ID NO: 4)
EIVLTQSPGTLSLSPGERATLSCQASQSISTALAWYQQKPGQAPRLLIYAASTLAS
GIPDRFSGSGSGTDFTLTISRLEPEDFAVYYCQQGYSSSNLDNVFGGGTKVEIK HC of Antibody 23C8 (SEQ ID NO: 5)
EVQLVESGGGLVQPGGSLRLSCAASGFDISKYNIQWVRQAPGKGLEWVGFINYG
GSAYYASRAKGRFTISRDDSKNSLYLQMNSLKTEDTAVYYCARGLSNSDLWGQ
GTLVTVSSASTKGPSVFPLAPCSRSTSESTAALGCLVKDYFPEPVTVSWNSGALTS
GVHTFPAVLQSSGLYSLSSVVTVPSSSLGTKTYTCNVDHKPSNTKVDKRVESKYG
PPCPPCPAPEAAGGPSVFLFPPKPKDTLMISRTPEVTCVVVDVSQEDPEVQFNWY
VDGVEVHNAKTKPREEQFNSTYRVVSVLTVLHQDWLNGKEYKCKVSNKGLPSSI
EKTISKAKGQPREPQVYTLPPSQEEMTKNQVSLTCLVKGFYPSDIAVEWESNGQP
ENNYKTTPPVLDSDGSFFLYSRLTVDKSRWQEGNVFSCSVMHEALHNHYTQKSL
SLSLG LC of Antibody 23C8 (SEQ ID NO: 6)
DIQMTQSPSSLSASVGDRVTITCQASQSISSWLSWYQQKPGKAPKLLIYRASTLAS
GVPSRFSGSGSGTDFTFTISSLQPEDIATYYCQSTYGGVVGSTSDDNPFGGGTKVEI
KRTVAAPSVFIFPPSDEQLKSGTASVVCLLNNFYPREAKVQWKVDNALQSGNSQ
ESVTEQDSKDSTYSLSSTLTLSKADYEKHKVYACEVTHQGLSSPVTKSFNRGEC HCVR of Antibody 23C8 (SEQ ID NO: 7)
EVQLVESGGGLVQPGGSLRLSCAASGEDISKYNIQWVRQAPGKGLEWVGFINYG
GSAYYASRAKGRFTISRDDSKNSLYLQMNSLKTEDTAVYYCARGLSNSDLWGQ
GTLVTVSS LCVR of Antibody 23C8 (SEQ ID NO: 8)
DIQMTQSPSSLSASVGDRVTITCQASQSISSWLSWYQQKPGKAPKLLIYRASTLAS
GVPSRFSGSGSGTDFTFTISSLQPEDIATYYCQSTYGGVVGSTSDDNPFGGGTKVEI
K HC of Antibody 25F7 (SEQ ID NO: 9)
QVQLVQSGAEVKKPGASVKVSCKASGFSLSTYAMNWRQAPGQGLEWMGIISD
DGTTYYATWAKGRVTMTRDTSTSTVYMELSSLRSEDTAVYYCARDAGAGGVQ
DYLTLWGQGTLVTVSSASTKGPSVFPLAPCSRSTSESTAALGCLVKDYFPEPVTV
SWNSGALTSGVHTFPAVLQSSGLYSLSSVVTVPSSSLGTKTYTCNVDHKPSNTKV
DKRVESKYGPPCPPCPAPEAAGGPSVFLEPPKPKDTLMISRTPEVTCVVVDVSQED
PEVQFNWYVDGVEVHNAKTKPREEQFNSTYRVVSVLTVLHQDWLNGKEYKCK
VSNKGLPSSIEKTISKAKGQPREPQVYTLPPSQEEMTKNQVSLTCLVKGFYPSDIA
VEWESNGQPENNYKTTPPVLDSDGSFFLYSRLTVDKSRWQEGNVFSCSVMHEAL
HNHYTQKSLSLSLG LC of Antibody 25F7 (SEQ ID NO: 10)
DIVMTQSPDSLAVSLGERATINCQASENIYNFLAWYQQKPGQPPKLLIYSASTLAS
GVPDRFSGSGSGTDFTLTISSLQAEDVAVYYCQQGSSNSNIDNPFGGGTKVEIKRT
VAAPSVFIFPPSDEQLKSGTASVVCLLNNFYPREAKVQWKVDNALQSGNSQESVT
EQDSKDSTYSLSSTLTLSKADYEKHKVYACEVTHQGLSSPVTKSFNRGEC HCVR of Antibody 25F7 (SEQ ID NO: 11)
QVQLVQSGAEVKKPGASVKVSCKASGFSLSTYAMNWVRQAPGQGLEWMGIISD
DGTTYYATWAKGRVTMTRDTSTSTVYMELSSLRSEDTAVYYCARDAGAGGVQ
DYLTLWGQGTLVTVSS LCVR of Antibody 25F7 (SEQ ID NO: 12)
DIVMTQSPDSLAVSLGERATINCQASENIYNFLAWYQQKPGQPPKLLIYSASTLAS
GVPDRFSGSGSGTDFTLTISSLQAEDVAVYYCQQGSSNSNIDNPFGGGTKVEIK

| Sequences |
|---|
| HCDR1 of Antibody 22B3 (SEQ ID NO: 13)<br>GIFSILSSYGVS<br><br>HCDR1 of Antibody 23C8 (SEQ ID NO: 14)<br>GFDISKYNIQ<br><br>HCDR1 of Antibody 25F7 (SEQ ID NO: 15)<br>GFSLSTYAMN<br><br>HCDR2 of Antibody 22B3 (SEQ ID NO: 16)<br>AISYDGITYYASWAKS<br><br>HCDR2 of Antibody 23C8 (SEQ ID NO: 17)<br>FINYGGSAYYASRAKG<br><br>HCDR2 of Antibody 25F7 (SEQ ID NO: 18)<br>IISDDGTTYYATWAKG<br><br>HCDR3 of Antibody 22B3 (SEQ ID NO: 19)<br>GDYYDDYVYVYALDI<br><br>HCDR3 of Antibody 23C8 (SEQ ID NO: 20)<br>GLSNSDL<br><br>HCDR3 of Antibody 25F7 (SEQ ID NO: 21)<br>DAGAGGVQDYLTL<br><br>LCDR1 of Antibody 22B3 (SEQ ID NO: 22)<br>QASQSISTALA<br><br>LCDR1 of Antibody 23C8 (SEQ ID NO: 23)<br>QASQSISSWLS<br><br>LCDR1 of Antibody 25F7 (SEQ ID NO: 24)<br>QASENIYNFLA<br><br>LCDR2 of Antibody 22B3 (SEQ ID NO: 25)<br>AASTLAS<br><br>LCDR2 of Antibody 23C8 (SEQ ID NO: 26)<br>RASTLAS<br><br>LCDR2 of Antibody 25F7 (SEQ ID NO: 27)<br>SASTLAS<br><br>LCDR3 of Antibody 22B3 (SEQ ID NO: 28)<br>QQGYSSSNLDNV<br><br>LCDR3 of Antibody 23C8 (SEQ ID NO: 29)<br>QSTYGGVVGSTSDDNP<br><br>LCDR3 of Antibody 25F7 (SEQ ID NO: 30)<br>QQGSSNSNIDNP<br>Human BTLA (SEQ ID NO: 31)<br>MKTLPANILGTGKLFWVFFLIPYLDIWNIFIGKESCDVQLYIKRQSEHSILAGDPFEL<br>ECPVKYCANRPHVTWCKLNGTTCVKLEDRQTSWKEEKNISFFILHFEPVLPNDNG<br>SYRCSANFQSNLIESHSTTLYVTDVKSASERPSKDEMASRPWLLYRLLPLGGLPLL<br>ITTCFCLFCCLRRHQGKQNELSDTAGREINLVDAHLKSEQTEASTRQNSQVLLSET<br>GIYDNDPDLCFRMQEGSEVYSNPCLEENKPGIVYASLNHSVIGPNSRLARNVKEA<br>PTEYASICVRS<br><br>Mouse Balbc BTLA (SEQ ID NO: 32)<br>MKTVPANILGTPRLFREFFILHLGLWSILCEKATKRNDEECEVQLNIKRNSKHSAW<br>TGELFKIECPVKYCVHRPNVTWCKHNGTIWVPLEVGPQLYTSWEENRSVPVFVL<br>HFKPIHLSDNGSYSCSTNFNSQVINSHSVTIHVRERTQNSSEHPLITVSDIPDATNAS<br>GPSTMEERPGRTWLLYTLLPLGALLLLLACVCLLCFLKRIQGKEKKPSDLAGRDT<br>NLVDIPASSRTNHQALPSGTGIYDNDPWSSMQDESELTISLQSERNNQGIVYASLN<br>HCVIGRNPRQENNMQEAPTEYASICVRS<br><br>Mouse C57BL6 BTLA (SEQ ID NO: 33)<br>MKTVPAMLGTPRLFREFFILHLGLWSILCEKATKRNDEECPVQLTITRNSKQSART<br>GELFKIQCPVKYCVHRPNVTWCKHNGTICVPLEVSPQLYTSWEENQSVPVFVLHF<br>KPIHLSDNGSYSCSTNFNSQVINSHSVTIHVTERTQNSSEHPLITVSDIPDATNASGP<br>STMEERPGRTWLLYTLLPLGALLLLLACVCLLCFLKRIQGK<br>EKKPSDLAGRDTNLVDIPASSRTNHQALPSGTGIYDNDPWSSMQDESELTISLQSE<br>RNNQGIVYASLNHCVIGRNPRQENNMQEAPTEYASICVRS |

-continued

Sequences

Cynomolgus Monkey BTLA (SEQ ID NO: 34)
MKTLPAMLGSGRLFWVVFLIPYLDIWNIHGKESCDVQLYIKRQSYHSIFAGDPFK
LECPVKYCAHRPQVTWCKLNGTTCVKLEGRHTSWKQEKNLSFFILHFEPVLPSD
NGSYRCSANFLSAIIESHSTTLYVTDVKSASERPSKDEMASRPWLLYSLLPLGGLP
LLITTCFCLFCFLRRHQGKQNELSDTTGREITLVDVPFKSEQTEASTRQNSQVLLSE
TGIYDNEPDFCFRMQEGSEVYSNPCLEENKPGIIYASLNHSIIGLNSRQARNVKEA
PTEYASICVRS Exemplified DNA for Expressing Antibody 22B3 Heavy Chain of SEQ ID NO: 1
(SEQ ID NO: 35)
caggtgcagctggtgcagtctggggctgaggtgaagaagcctggggcctcagtgaaggtttcctgcaaggcatctggattctcc
ctcagtagctatggagtgagctgggtgcgacaggcccctggacaagggcttgagtggatgggagccattagttatgatggtatta
catactacgcgagctgggcgaaaagcagagtcaccatgaccagggacacgtccacgagcacagtctacatggagctgagcag
cctgagatctgaggacacggccgtgtattactgtgcgagaggggactactacgatgattatgtttatgtttatgctttagacatctgg
ggccagggcaccctggtcaccgtctcctcagcttctaccaagggcccatcggtcttccccctagcgccctgctccaggagcacc
tccgagagcacagccgccctgggctgcctggtcaaggactacttccccgaaccggtgacggtgtcgtggaactcaggcgccct
gaccagcggcgtgcacaccttcccggctgtcctacagtcctcaggactctactccctcagcagcgtggtgaccgtgccctccag
cagcttgggcacgaagacctacacctgcaacgtagatcacaagcccagcaacaccaaggtggacaagagagttgagtccaaa
tatggtccccatgcccacctgcccacctgaggccgccggggaccatcagtcttcctgttccccccaaaacccaagga
cactctcatgatctcccggacccctgaggtcacgtgcgtggtggtggacgtgagccaggaagaccccgaggtccagttcaactg
gtacgtggatggcgtggaggtgcataatgccaagacaaagccgcggggaggagcagttcaacagcacgtaccgtgtggtcagc
gtcctcaccgtcctgcaccaggactggctgaacggcaaggagtacaagtgcaaggtctccaacaaagcctcccgtcctccatc
gagaaaaccatctccaaagccaaagggcagccccgagagccacaggtgtacaccctgcccccatcccaggaggagatgacc
aagaaccaggtcagcctgacctgcctggtcaaaggcttctaccccagcgacatcgccgtggagtgggaaagcaatgggcagc
cggagaacaactacaagaccacgcctcccgtgctggactccgacggctccttcttcctctacagcaggctaaccgtggacaaga
gcaggtggcaggaggggaatgtcttctcatgctccgtgatgcatgaggctctgcacaaccactacacacagaagagcctctccc
tgtctctgggt Exemplified DNA for Expressing Antibody 22B3 Light Chain of SEQ ID NO: 2 (SEQ
ID NO: 36)
Gaaattgtgttgacgcagtaccaggcaccagtattgtaccagggaaagagccaccactcctgccaggccagtcagagc
attagtactgcattagcctggtaccagcagaaacctggccaggctcccaggctcctcatctatgctgcatccactaggcatctgg
catcccagacaggttcagtggcagtgggtagggacagacttcactctcaccatcagcagactggagcctgaagattttgcagtg
tattactgtcaacaggggttatagtagtagtaatcttgataatgttttcggcggagggaccaaggtggagatcaaacggaccgtggct
gcaccatctgtcttcatcttcccgccatctgatgagcagttgaaatctggaactgcctagttgtgtgcctgctgaataacttctatccc
agagaggccaaagtacagtggaaggtggataacgccaccctacagcgggtaactcccaggagagtgtcacagagcaggacagc
aaggacagcacctacagcctcagcagcaccctgacgctgagcaaagcagactacgagaaacacaaagtctacgcctgcgaa
gtcacccatcagggcctgagctcgcccgtcacaaagagcttcaacaggggagagtgc Exemplified DNA for Expressing Antibody 23C8 Heavy Chain of SEQ ID NO: 5
(SEQ ID NO: 37)
gaggtgcagaggtggagtaggggggaggcttggtccagcctggagggtccctgagactacctgtgcagcctaggattcgac
atcagtaagtacaacatccaatgggtccgccaggctccagggaaggggctggagtgggttggcttcattaattatggtggtagcg
catactacgcgagccgggcgaaaggcagagtcaccatctcaagagatgattcaaagaacctcactgtatctgcaaatgaacagcct
gaaaaccgaggacacggccgtgtattactgtgctagaggactaagtaatagcgacctaggggccagggcaccaggtcaccg
tctcctcagcttctaccaagggcccatcggtcttccccgctagcgccctgaccaggagcacctccgagagcacagccgccagg
gctgcctggtcaaggactacttccccgaaccggtgacggtgtcgtggaactcaggcgccctgaccagcggcgtgcacaccttc
ccggctgtcctacagtcctcaggactctactccctcagcagcgtggtgaccgtgccctccagcagcttgggcacgaagacctac
acctgcaacgtagatcacaagcccagcaacaccaaggtggacaagagagttgagtccaaatatggtccccatgcccaccag
cccagcacctgaggccgccggggaccatcagtcttcctgttccccccaaaacccaaggacactctcatgatctcccggaccccc
tgaggtcacgtgcgtggtggtggacgtgagccaggaagaccccgaggtccagttcaactggtacgtggatggcgtggaggtg
cataatgccaagacaaagccgcggaggagcagttcaacagcacgtaccgtgtggtcagcgtcctcaccgtcctgcaccagg
actggctgaacggcaaggagtacaagtgcaaggtctccaacaaagcctcccgtcctccatcgagaaaaccatctccaaagcc
aaagggcagccccgagagccacaggtgtacaccagccccatcccaggaggagatgaccaagaaccaggtcagcctgacc
tgcctggtcaaaggcttctaccccagcgacatcgccgtggagtgggaaagcaatgggcagccggagaacaactacaagacca
cgcctcccgtgctggactccgacggctccttcttcctctacagcaggctaaccgtggacaagagcaggtggcaggaggggaat
gtcttctcatgaccgtgatgcatgaggactgcacaaccactacacacagaagagcctaccagtactgggt Exemplified DNA for Expressing Antibody 23C8 Light Chain of SEQ ID NO: 6 (SEQ
ID NO: 38)
gacatccagatgacccagtctccatcctccctgtctgcatctgtaggagacagagtcaccatcacttgccaggccagtcagagca
ttagtagttggttatcctggtatcagcagaaaccagggaaagcccctaagctcctgatctacagggcatccactctggcatctggg
gtcccatcaaggttcagtggaagtggatctgggacagattttactttcaccatcagcagcctgcagcctgaagatattgcaacatat
tactgtcaatccacttatggtggtgttgttggcagtactagtgatgataatccttttcggcggagggaccaaggtggagatcaaacg
gaccgtggctgcaccatctgtcttcatcttcccgccatctgatgagcagttgaaatctggaactgcctctgttgtgtgcctgctgaat
aacttctatcccagagaggccaaagtacagtggaaggtggataacgccctccaatcgggtaactcccaggagagtgtcacaga
gcaggacagcaaggacagcacctacagcctcagcagcaccctgacgctgagcaaagcagactacgagaaacacaaagtcta
cgcctgcgaagtcacccatcagggcctgagctcgcccgtcacaaagagcttcaacaggggagagtgc Exemplified DNA for Expressing Antibody 25F7 Heavy Chain of SEQ ID NO: 9
(SEQ ID NO: 39)
caggtgcagctggtgcagtctggggctgaggtgaagaagcctggggcctcagtgaaggtttcctgcaaggcatctggattctcc
ctcagtacctatgcaatgaactgggtgcgacaggcccctggacaagggcttgagtggatgggaatcattagtgatgatggtacca
catactacgcgacctgggcgaaaggcagagtcaccatgaccagggacacgtccacgagcacagtctacatggagctgagcag
cctgagatctgaggacacggccgtgtattactgtgcgagagatgctggtgctggtggtgtccaagactacttaaccttgggggc
cagggcaccctggtcaccgtctcctcagcttctaccaagggcccatcggtcttcccgctagcgccctgctccaggagcacctcc

```
gagagcacagccgccctgggctgcctggtcaaggactacttccccgaaccggtgacggtgtcgtggaactcaggcgccctga
ccagcggcgtgcacaccttcccggctgtcctacagtcctcaggactctactccctcagcagcgtggtgaccgtgccctccagca
gcttgggcacgaagacctacacctgcaacgtagatcacaagcccagcaacaccaaggtggacaagagagtttgagtccaaatat
ggtcccccatgcccaccctgcccagcacctgaggccgccggggggaccatcagtcttcctgttccccccaaaacccaaggacac
tctcatgatctcccggacccctgaggtcacgtgcgtggtggtggacgtgagccaggaagaccccgaggtccagttcaactggta
cgtggatggcgtggaggtgcataatgccaagacaaagccgcgggaggagcagttcaacagcacgtaccgtgtggtcagcgtc
ctcaccgtcctgcaccaggactggctgaacggcaaggagtacaagtgcaaggtctccaacaaaggcctcccgtcctccatcga
gaaaaccatctccaaagccaaagggcagccccgagagccacaggtgtacaccctgcccccatcccaggaggagatgaccaa
gaaccaggtcagcctgacctgcctggtcaaaggcttctaccccagcgacatcgccgtggagtgggaaagcaatgggcagccg
gagaacaactacaagaccacgcctcccgtgctggactccgacggctccttcttcctctacagcaggctaaccgtggacaagagc
aggtggcaggaggggaatgtcttctcatgctccgtgatgcatgaggctctgcacaaccactacacacagaagagcctctccctgt
ctctgggt
```

Exemplified DNA for Expressing Antibody 25F7 Light Chain of SEQ ID NO: 10
(SEQ ID NO: 40)
```
Gacatcgtgatgacccagtaccagactccctggctgtgtactgggcgagagggccaccatcaactgccaggccagtgagaa
tatttacaacttttttggcctggtaccagcagaaaccaggacagcctcctaagagctcatttactagcatccactaggcatctggg
gtccctgaccgattcagtggcagcgggtagggacagatttcactctcaccatcagcagcctgcaggctgaagatgtggcagttt
attactgtcaacaggttctagtaatagtaatattgataatcctttcggcggagggaccaaggtggagatcaaacgaccgtggct
gcaccatctgtcttcatcttcccgccatctgatgagcagttgaaatctggaactgcctagttgtgtgcctgctgaataacttctatccc
agagaggccaaagtacagtggaaggtggataacgccaccaatcgggtaactcccaggagagtgtcacagagcaggacagc
aaggacagcacctacagcctcagcagcacctgacgctgagcaaagcagactacgagaaacacaaagtctacgcctgcgaa
gtcacccatcagggcctgagctcgcccgtcacaaagagcttcaacaggggagagtgc
```

Human HVEM (SEQ ID NO: 41)
```
MEPPGDWGPPPWRSTPKTDVLRLVLYLTFLGAPCYAPALPSCKEDEYPVGSECCP
KCSPGYRVKEACGELTGTVCEPCPPGTYIAHLNGLSKCLQCQMCDPAMGLRASR
NCSRTENAVCGCSPGHFCIVQDGDHCAACRAYATSSPGQRVQKGGTESQDTLCQ
NCPPGTFSPNGTLEECQHQTKCSWLVTKAGAGTSSSHWVWWFLSGSLVIVIVCST
VGLIICVKRRKPRGDVVKVIVSVQRKRQEAEGEATVIEALQAPPDVTTVAVEETIP
SFTGRSPNH
```

We claim:

1. An antibody that binds BTLA, comprising HCDR1 having the amino acid sequence of SEQ ID NO: 13, HCDR2 having the amino acid sequence of SEQ ID NO: 16, HCDR3 having the amino acid sequence of SEQ ID NO: 19, LCDR1 having the amino acid sequence of SEQ ID NO: 22, LCDR2 having the amino acid sequence of SEQ ID NO: 25, and LCDR3 having the amino acid sequence of SEQ ID NO: 28.

2. The antibody of claim 1, comprising a heavy chain variable region (HCVR) having the amino acid sequence of SEQ ID NO: 3, and a light chain variable region (LCVR) having the amino acid sequence of SEQ ID NO: 4.

3. The antibody of claim 1, comprising a heavy chain (HC) having the amino acid sequence of SEQ ID NO: 1, and a light chain (LC) having the amino acid sequence of SEQ ID NO: 2.

4. The antibody of claim 1, comprising two HC and two LC, wherein each HC has the amino acid sequence of SEQ ID NO: 1, and each light chain (LC) has the amino acid sequence of SEQ ID NO: 2.

5. A pharmaceutical composition comprising the antibody of claim 1, and one or more pharmaceutically acceptable carriers, diluents, or excipients.

6. An antibody obtainable by a) cultivating a mammalian cell comprising a DNA molecule comprising a polynucleotide sequence that encodes the antibody heavy chain having the amino acid sequence of SEQ ID NO: 1 and a polynucleotide sequence that encodes the antibody light chain having the amino acid sequence of SEQ ID NO: 2 under conditions such that the antibody is expressed, and b) recovering the expressed antibody.

7. A method of treating a patient having a rheumatic disease selected from at least one of lupus nephritis, systemic lupus erythematosus, and rheumatoid arthritis, comprising administering to the patient an effective amount of an antibody of claim 1.

8. A method of treating a patient having a dermatology disease selected from at least one of atopic dermatitis and psoriasis, comprising administering to the patient an effective amount of an antibody of claim 1.

9. A method of treating a patient having multiple sclerosis comprising administering to the patient an effective amount of an antibody of claim 1.

* * * * *